United States Patent [19]

Mullis et al.

[11] Patent Number: 4,800,159
[45] Date of Patent: * Jan. 24, 1989

[54] PROCESS FOR AMPLIFYING, DETECTING, AND/OR CLONING NUCLEIC ACID SEQUENCES

[75] Inventors: Kary B. Mullis, La Jolla; Henry A. Erlich, Oakland; Norman Arnheim, Woodland Hills; Glenn T. Horn, Emeryville; Randall K. Saiki, Richmond; Stephen J. Scharf, Berkeley, all of Calif.

[73] Assignee: Cetus Corporation, Emeryville, Calif.

[ * ] Notice: The portion of the term of this patent subsequent to Jul. 28, 2004 has been disclaimed.

[21] Appl. No.: 943,948

[22] Filed: Dec. 17, 1986

Related U.S. Application Data

[60] Continuation of Ser. No. 828,144, Feb. 7, 1986, Pat. No. 4,683,195, which is a continuation-in-part of Ser. No. 824,044, Jan. 30, 1986, abandoned, which is a division of Ser. No. 791,308, Oct. 25, 1985, Pat. No. 4,683,202, which is a continuation-in-part of Ser. No. 716,975, Mar. 28, 1985, abandoned.

[51] Int. Cl.$^4$ .............. C12N 15/00; C12P 19/34; C07H 21/04
[52] U.S. Cl. ................... 435/172.3; 435/91; 435/172.1; 435/320; 536/27; 935/17; 935/18
[58] Field of Search ............ 435/91, 172.1, 172.3; 935/17, 18; 536/27

[56] References Cited

U.S. PATENT DOCUMENTS

| | | | |
|---|---|---|---|
| 4,237,224 | 12/1980 | Cohen et al. | 435/172.3 |
| 4,683,195 | 7/1987 | Mullis et al. | 435/172.3 |
| 4,683,202 | 7/1987 | Mullis | 435/172.3 |

OTHER PUBLICATIONS

Rossi et al., J. Biol. Chem. 257: 9226–9229 (1982).
E. Taparowsky et al., Cell, 34:581–586 (1983).

*Primary Examiner*—James Martinell
*Attorney, Agent, or Firm*—Kevin R. Kaster; Janet E. Hasak; Albert P. Halluin

[57] ABSTRACT

The present invention is directed to a process for amplifying and detecting any target nucleic acid sequence contained in a nucleic acid or mixture thereof. The process comprises treating separate complementary strands of the nucleic acid with a molar excess of two oligonucleotide primers, extending the primers to form complementary primer extension products which act as templates for synthesizing the desired nucleic acid sequence, and detecting the sequence so amplified. The steps of the reaction may be carried out stepwise or simultaneously and can be repeated as often as desired.

In addition, a specific nucleic acid sequence may be cloned into a vector by using primers to amplify the sequence, which contain restriction sites on their non-complementary ends, and a nucleic acid fragment may be prepared from an existing shorter fragment using the amplification process.

6 Claims, 11 Drawing Sheets

FIG. 1

Double-Stranded 94-bp Sequence

```
TTTGC  TTCTGACACA  ACTGTGTTCA  CTAGCAACCT ──▶
AAACG  AAGACTGTGT  TGACACAAGT  GATCGTTGGA
```

```
              NcoI        HinfI MstII
               V            V    V
CAAACAGACA  CCATGGTGCA  CCTGACTCCT  GAGGAGAAGT ──▶
GTTTGTCTGT  GGTACCACGT  GGACTGAGGA  CTCCTCTTCA
                                       ↑
                                    Allelic base
                                    pair DNA
                                    polymorphism
```

```
CTGCCGTTAC  TGCCCTGTG
GACGGCAATG  ACGGGACAC
```

FIG. 6

```
             =========-----
β^A   CATGGTGCACCTGACTCCTGAGGAGAAGTCTGCCGTTACTGCCCTGTGGGGCAAGGTGAA
      GTACCACGTGGACTGAGGACTCCTCTTCAGACGGCAATGACGGGACACCCCGTTCCACTT
             ==========-----
```

```
             =====   *
β^S   CATGGTGCACCTGACTCCTGTGGAGAAGTCTGCCGTTACTGCCCTGTGGGGCAAGGTGAA
      GTACCACGTGGACTGAGGACACCTCTTCAGACGGCAATGACGGGACACCCCGTTCCACTT
             =====
```

* Marks the mutation (A to T) in the sickle cell gene which disrupts the Dde I site

FIG. 4-1 Human Betaglobin

```
        101         111         121         131***       141         151         161         171         181         191         201         211         221
...CCATCTATTG CTTACATTTG CTTCTGACAC AACTGTGTTC ACTAGCAACC ACCTGACTCC TGAGGAGAAG TCTGCCCTTA CTGCCCTGTG GGGCAAGGTG AAGTTGGTGG..
...GGTAGATAAC GAATGTAAAC GAAGACTGTG TTGACACAAG TGATCGTTGG TGGACTGAGG ACTCCTCTTC AGACGGGAAT GACGGGACAC CCCGTTCCAC TTCAACCACC..

CACAGGGCAGTAACG   PCO1
TTTGCTTCTGACACA   PCO2

; denature, re-anneal
                                                                    ;—>

...CCATCTATTG CTTACATTTG CTTCTGACAC AACTGTGTTC ACTAGCAACC ACCTGACTCC TGAGGAGAAG TCTGCCCTTA CTGCCCTGTG GGGCAAGGTG AAGTTGGTGG.
                                                                                          ||||          |||||||||||
                                                                                 extends <----  GCAAT GACGGGACAC  5'  PCO1

5'  PCO2  TTTG CTTCTGACAC A ---> extends
           ||||  ||||||||||
...GGTAGATAAC GAATGTAAAC GAAGACTGTG TTGACACAAG TGATCGTTGG TGGACTGAGG ACTCCTCTTC AGACGGGAAT GACGGGACAC CCCGTTCCAC TTCAACCACC..

Polymerase, dNTPs
                                                                    —>

TTTG CTTCTGACAC AACTGTGTTC ACTAGCAACC ACCTGACTCC TGAGGAGAAG TCTGCCCTTA CTGCCCTGTG GGGCAAGGTG AAGTTGGTGG.
       ||||  |||||||||| |||||||||| |||||||||| |||||||||| |||||||||| |||||||||| |||||||||| |||||||||| ||||||||||
...GGTAGATAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC..

...CCATCTATTG CTTACATTTG CTTCTGACAC AACTGTGTTC ACTAGCAACC ACCTGACTCC TGAGGAGAAG TCTGCCCTTA CTGCCCTGTG GGGCAAGGTG AAGTTGGTGG.
   |||||||||| |||||||||| |||||||||| |||||||||| |||||||||| |||||||||| |||||||||| ||||          |||||||||||
                                                                                 extends <----  GCAAT GACGGGACAC  5'  PCO1

5'  PCO2  TTTG CTTCTGACAC A ---> extends
           ||||  ||||||||||   :
...GGTAGATAAC GAATGTAAAC GAACACTGTG TTGACACAAG TGATCGTTGG TGGACTGAGG ACTCCTCTTC AGACGGCAAT GACGGGACAC CCCGTTCCAC TTCAACCACC..
```

CYCLES 1, 2

FIG.4-2-1

```
0  CCATCTATTG CTTACATTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
2  :::::::::: :::::::::: :::::::::: :::::::::: :::::::::: :::::::::: :::::::::: :::::::::: :::::::::: :::::::::: ::::::::::
   GGTAGATAAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC

TTTG CTTCTGACAC AACTGTGTTC ACTAGCAACC ACCTGACTCC TGAGGAGAAG TCTGCCGTTA CTGCCCTGTG
2                        :::: :::::::::: :::::::::: :::::::::: :::::::::: :::::::::: :::::::::: ::::::::::
1  GGTAGATAAAC GAATGTAAAC GAAGACTGTG TTGACACAAG TGATCGTTGG TGGACTGAGG ACTCCTCTTC AGACGGCAAT GACGGGACAC

TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
1                        :::: :::::::::: :::::::::: :::::::::: :::::::::: :::::::::: :::::::::: :::::::::: :::::::::: ::::::::::
2                        AAAC GAAGACTGTG TTGACACAAG TGATCGTTGG TGGACTGAGG ACTCCTCTTC AGACGGCAAT GACGGGACAC

TTTG CTTCTGACAC AACTGTGTTC ACTAGCAACC ACCTGACTCC TGAGGAGAAG TCTGCCGTTA CTGCCCTGTG GGGCAAGGTG AAGTTGGTGG...
2                        :::: :::::::::: :::::::::: :::::::::: :::::::::: :::::::::: :::::::::: :::::::::: :::::::::: ::::::::::
0  GGTAGATAAAC GAATGTAAAC GAAGACTGTG TTGACACAAG TGATCGTTGG TGGACTGAGG ACTCCTCTTC AGACGGCAAT GACGGGACAC CCCGTTCCAC TTCAACCACC
```

Polymerase, dNTPs denature, re-anneal

![Figure showing DNA sequence amplification via PCR cycles]

| N | template | long product | short product =2(expN)-N-1 |
|---|----------|--------------|------|
| 0 | 1 | 0 | 0 |
| 1 | 1 | 1 | 0 |
| 5 | 1 | 5 | 26 |
| 10 | 1 | 10 | 1013 |
| 15 | 1 | 15 | 32,752 |
| 20 | 1 | 20 | 1,048,555 |

COPIES OF DNA SEQUENCE AFTER N CYCLES

A B C D
 8-MER
 3-MER
FIG.9

PROCESS FOR AMPLIFYING, DETECTING, AND/OR CLONING NUCLEIC ACID SEQUENCES

FIELD OF THE INVENTION

The present invention relates to a process for amplifying existing nucleic acid sequences if they are present in a test sample and detecting them if present by using a probe. More specifically, it relates to a process for producing any particular nuclei acid sequence from a given sequence of DNA or RNA in amounts which are large compared to the amount initially present so as to facilitate detection of the sequences. The DNA or RNA may be single- or doublestranded, and may be a relatively pure species or a component of a mixture of nucleic acids. The process of the invention utilizes a repetitive reaction to accomplish the amplification of the desired nucleic acid sequence.

BACKGROUND OF THE INVENTION

For diagnostic applications in particular, the target nucleic acid sequence may be only a small portion of the DNA or RNA in question, so that it may be difficult to detect its presence using nonisotopically labeled or end-labeled oligonucleotide probes. Much effort is being expended in increasing the sensitivity of the probe detection systems, but little research has been conducted on amplifying the target sequence so that it is present in quantities sufficient to be readily detectable using currently available methods.

Several methods have been described in the literature for the synthesis of nucleic acids de novo or from an existing sequence. These methods are capable of producing large amounts of a given nucleic acid of completely specified sequence.

One known method for synthesizing nucleic acids de novo involves the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared which can then be joined together to form longer nucleic acids. For a description of this method, see Narang, S.A., et al., *Meth. Enzymol.*, 68, 90 (1979) and U.S. Pat. No. 4,356,270. The patent describes the synthesis and cloning of the somatostatin gene.

A second type of organic synthesis is the phosphodiester method, which has been utilized to prepare a tRNA gene. See Brown, E.L., et al., *Meth. Enzymol.*, 68, 109 (1979) for a description of this method. As in the phosphotriester method, the phosphodiester method involves synthesis of oligonucleotides which are subsequently joined together to form the desired nucleic acid.

Although the above processes for de novo synthesis may be utilized to synthesize long strands of nucleic acid, they are not very practical to use for the synthesis of large amounts of a nucleic acid. Both processes are laborious and time-consuming, require expensive equipment and reagents, and have a low overall efficiency. The low overall efficiency may be caused by the inefficiencies of the synthesis of the oligonucleotides and of the joining reactions. In the synthesis of a long nucleic acid, or even in the synthesis of a large amount of a shorter nucleic acid, many oligonucleotides would need to be synthesized and many joining reactions would be required. Consequently, these methods would not be practical for synthesizing large amounts of any desired nucleic acid.

Methods also exist for producing nucleic acids in large amounts from small amounts of the initial existing nucleic acid. These methods involve the cloning of a nucleic acid in the appropriate host system, where the desired nucleic acid is inserted into an appropriate vector which is used to transform the host. When the host is cultured the vector is replicated, and hence more copies of the desired nuclei acid are produced. For a brief description of subcloning nucleic acid fragments, see Maniatis, T., et al., *Molecular Cloning: A Laboratory Manual*, Cold Spring Harbor Laboratory, pp. 390-401 (1982). See also the techniques described in U.S. Pat. Nos. 4,416,988 and 4,403,036.

A third method for synthesizing nucleic acids, described in U.S. Pat. No. 4,293,652, is a hybrid of the above-described organic synthesis and molecular cloning methods. In this process, the appropriate number of oligonucleotides to make up the desired nucleic acid sequence is organically synthesized and inserted sequentially into a vector which is amplified by growth prior to each succeeding insertion.

The present invention bears some similarity to the molecular cloning method; however, it does not involve the propagation of any organism and thereby avoids the possible hazards or inconvenience which this entails. The present invention also does not require synthesis of nucleic acid sequences unrelated to the desired sequence, and thereby the present invention obviates the need for extensive purification of the product from a complicated biological mixture.

SUMMARY OF THE INVENTION

The present invention resides in a process for amplifying one or more specific nucleic acid sequences present in a nucleic acid or mixture thereof using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. This method is expected to be more efficient than the methods described above for producing large amounts of nucleic acid from a target sequence and to produce such nucleic acid in a comparatively short period of time. The present method is especially useful for amplifying rare species of nucleic acid present in a mixture of nucleic acids for effective detection of such species.

More specifically, the present invention provides a process for detecting the presence or absence of at least one specific nucleic acid sequence in a sample containing a nucleic acid or mixture of nucleic acids, or distinguishing between two different forms of sequences in said sample, wherein the sample is suspected of containing said sequence or sequences, which process comprises:

(a) treating the sample with one oligonucleotide primer for each strand of each different specific sequence suspected of being present in the sample, under hybridizing conditions such that for each strand of each different sequence to be detected an extension product of each primer is synthesized which is complementary to each nucleic acid strand, wherein said primer or primers are selected so as to be substantially complementary to each strand of each specific sequence such that the extension product synthesized from one primer, when it is separated from its complement, can serve as a template for synthesis of the extension product of the other primer;

(b) treating the sample under denaturing conditions to separate the primer extension products from their templates if the sequence or sequences to be detected are present;

(c) treating the sample with oligonucleotide primers such that a primer extension product is synthesized using each of the single strands produced in step (b) as a template, resulting in amplification of the specific nucleic acid sequence or sequences if present;

(d) adding to the product of step (c) a labeled probe capable of hybridizing to said sequence being detected or a mutation thereof; and (e) determining whether said hybridization has occurred.

The steps (a)–(c) may be conducted sequentially or simultaneously. In addition, steps (b) and (c) may be repeated until the desired level of sequence amplification is obtained.

In other embodiments the invention relates to diagnostic kits for the detection of at least one specific nucleic acid sequence in a sample containing one or more nucleic acids at least one of which nucleic acid is suspected of containing said sequence, which kit comprises, in packaged form, a multicontainer unit having (a) one container for each oligonucleotide primer for each strand of each different sequence to be detected, which primer or primers are substantially complementary to each strand of each specific nucleic acid sequence such that an extension product synthesized from one primer, when it is separated from its complement, can serve as a template for the synthesis of the extension product of the other primer;

(b) a container containing an agent for polymerization;

(c) a container for each of four different nucleoside triphosphates;

(d) a container containing a probe capable of detecting the presence of said sequence in said sample; and (e) a container containing means for detecting hybrids of said probe and said sequence.

In yet another embodiment, the invention relates to a process for cloning into a vector a specific nucleic acid sequence contained in a nucleic acid or a mixture of nucleic acids, which process comprises:

(a) treating the nucleic acid(s) with one oligonucleotide primer for each strand of each different specific sequence being amplified, under conditions such that for each strand of each different sequence being amplified an extension product of each primer is synthesized which is complementary to each nucleic acid strand, wherein said primer or primers are selected so as to be substantially complementary to each strand of each specific sequence such that the extension product synthesized form one primer, when it is separated from its complement, can serve as a template for synthesis of the extension product of the other primer, and wherein said primer or primers each contain a restriction site on its 5' end which is the same as or different from the restriction site(s) on the other primer(s);

(b) separating the primer extension products from the templates on which they are synthesized to produce single-stranded molecules;

(c) treating the single-stranded molecules generated from step (b) with oligonucleotide primers such that a primer extension product is synthesized using each of the single strands produced in step (b) as a template, wherein depending on the particular sequence being amplified, steps (a) and (c) are carried out in the presence of from 0 up to an effective amount of dimethylsulfoxide or at a temperature of up to about 45° C.;

(d) adding to the product of step (c) a restriction enzyme for each of said restriction sites to obtain cleaved products in a restriction digest; and (e) ligating the cleaved product(s) into one or more cloning vectors.

In yet another embodiment, the invention herein relates to a process for synthesizing a nucleic acid fragment from an existing nucleic acid fragment having fewer nucleotides than the fragment being synthesized and two oligonucleotide primers, wherein the nucleic acid being synthesized is comprised of a left segment, a core segment and a right segment, and wherein the core segment represents at least substantially the nucleotide sequence of said existing nucleic acid fragment, and the right and left segments represent the sequence nucleotide present in the 5' ends of the two primers, the 3' ends of which are complementary or substantially complementary to the 3' ends of the single strands produced by separating the strands of said existing nucleic acid fragment, which process comprises:

(a) treating the strands of said existing fragment with two oligonucleotide primers under conditions such that an extension product of each primer is synthesized which is complementary to each nucleic acid strand, wherein said primers are selected so as to be substantially complementary to the 3' end of each strand of said existing fragment such that the extension product synthesized from one primer, when it is separated from its complement, can serve as a template for synthesis of the extension product of the other primer, and wherein each primer contains, at its 5' end, a sequence of nucleotides which are not complementary to said existing fragment and which correspond to the two ends of the nucleic acid fragment being synthesized;

(b) separating the primer extension products from the templates on which they were synthesized to produce single-stranded molecules;

(c) treating the single-stranded molecules generated from step (b) with the primers of step (a) under conditions such that a primer extension product is synthesized using each of the single strands produced in step (b) as a template so as to produce two intermediate double-stranded nucleic acid molecules, into each of which has been incorporated the nucleotide sequence present in the 5' end of one of the oligonucleotide primers, and two full-length doublestranded nucleic acid molecules, into each of which has been incorporated the nucleotide sequence present in the 5' ends of both of the oligonucleotide primers;

(d) repeating steps (b) and (c) for a sufficient number of times to produce the full-length double-stranded molecule in an effective amount;

(e) treating the strands of the product of step (d) with two primers so as to lengthen the product of step (d) on both ends; and (f) repeating steps (a)–(d) using the product of step (d) as the core fragment and two oligonucleotide primers which are complementary or substantially complementary to the 3' ends of the single strands produced by separating the strands of the product of step (d).

The core fragment may be obtained by the steps comprising:

(a) reacting two oligonucleotides, each of which contain at their 3' ends a nucleotide sequence which is complementary to the other oligonucleotide at its 3' end, and which are non-complementary to each other at their 5' ends, with an agent for polymerization and four nucleoside triphosphates under conditions such that an extension product of each oligonucleotide is synthesized which is complementary to each nucleic acid strand;

(b) separating the extension products from the templates on which they are synthesized to produce single-stranded molecules; and (c) treating the single-stranded molecules generated from step (b) with the oligonucleotides of step (a) under conditions such that a primer extension product is synthesized using each of the single strands produced in step (b) as a template, resulting in amplification of the core fragment.

BRIEF DESCRIPTION OF THE DRAWINGS

FIG. 1 illustrates a 94 base pair length sequence of human β-globin desired to be amplified. The single base pair change which is associated with sickle cell anemia is depicted beneath the 94-mer.

FIG. 4 illustrates in detail the steps and products of the polymerase chain reaction for amplification of the desired 94-mer sequence of human β-globin for three cycles using two oligonucleotide primers.

FIG. 6 illustrates the sequence of the normal ($\beta^A$) and sickle cell ($\beta^S$) β-globin genes in the region of the DdeI and HinfI restriction sites, where the single lines for $\beta^A$ mark the position of the DdeI site (CTGAG) and the double bars for $\beta^A$ and $\beta^S$ mark the position of the HinfI site (GACTC).

FIG. 9 illustrates a photograph of an ethidium bromidestained polyacrylamide gel demonstrating the use of the same 40-mer probe as in FIG. 7 to specifically characterize the beta-globin alleles present in samples of whole human DNA which have been subjected to amplification, hybridization with the probe, and sequential digestion with DdeI and HinFfI.

DETAILED DESCRIPTION OF THE PREFERRED EMBODIMENTS

Figure 2:
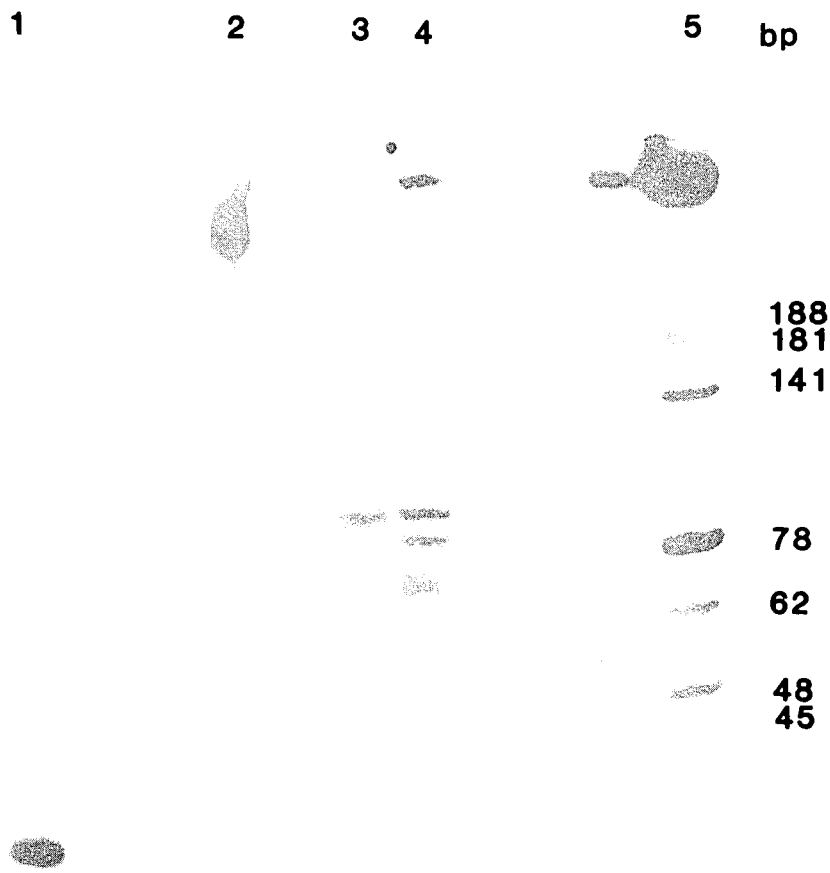
FIG. 2 illustrates a photograph of an ethidium bromidestained polyacrylamide gel demonstrating amplification of the 94-mer contained in human wild-type DNA and in a plasmid containing a 1.9 kb BamHI fragment of the normal β-globin gene (pBR328:HbA).

The term "oligonucleotide" as used herein in referring to primers, probes, oligomer fragments to be detected, oligomer controls and unlabeled blocking oligomers is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15-25 or more nucleotides, although it may contain fewer nucleotides. Short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

As used herein, the terms "restriction endonucleases" and "restriction enzymes" refer to bacterial enzymes each of which cut double-stranded DNA at or near a specific nucleotide sequence.

As used herein, the term "DNA polymorphism" refers to the condition in which two or more different nucleotide sequences coexist in the same interbreeding population in a DNA sequence.

The term "restriction fragment length polymorphism" ("RFLP") refers to the differences in DNA nucleotide sequences that are randomly distributed throughout the entire human genome and that produce different restriction endonuclease patterns.

The present invention is directed to a process for amplifying any one of more desired specific nucleic acid sequences suspected of being in a nucleic acid. Because large amounts of a specific sequence may be produced by this process, the present invention may be used for improving the efficiency of cloning DNA or messenger RNA and for amplifying a target sequence to facilitate detection thereof.

In general, the present process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employed.

Any source of nucleic acid, in purified or nonpurified form, can be utilized as the starting nucleic acid or acids, provided it is suspected of containing the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amlified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the $\beta$-globin gene contained in whole human DNA or a portion of nucleic acic sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al., Molecular Cloning: A Laboratory Manual, (New York: Cold Spring Harbor Laboratory, 1982), pp. 280-281.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater can be the specificity of the primers for the target nucleic acid sequence, and thus the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phosphotriester and phosphodiester methods described above, or automated embodiments thereof. In one such automated embodiment diethylphosphoramidites are used as starting materials and may be synthesized as described by Beaucage et al., *Tetrahedron Letters* (1981), 22:1859-1862. One method for synthesizing oligonucleotides on a modified solid support is described in U.S. Pat. No. 4,458,066. It is also possible to use a primer which has been isolated from a biological source (such as a restriction endonuclease digest).

The specific nuclei acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the nucleic acid involves heating the nucleic acid until it is completely (>99%) denatured. Typical heat denaturation may involve temperatures ranging from about 80° to 105° C. for times ranging from about 1 to 10 minutes. Strand separation may also be induced by an enzyme from the class of enzymes known as helicases or the enzyme ReCA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63-67, and techniques for using RecA are reviewed in C. Radding, *Ann. Rev. Genetics*, 16:405-37 (1982).

If the original nucleic acid containing the sequence to be amplified is single stranded, its complement is synthesized by adding one or two oligonucleotide primers thereto. If an appropriate single primer is added, a primer extension product is synthesized in the presence of the primer, an agent for polymerization and the four nucleotides described below. The product will be partially complementary to the single-stranded nucleic acid and will hybridize with the nucleic acid strand to form a duplex of unequal length strands that may then be separated into single strands as described above to produce two single separated complementary strands. Alternatively, two appropriate primers may be added to the single-stranded nucleic acid and the reaction carried out.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture in adequate amounts and the resulting solution is heated to about 90°–100° C. for from about 1 to 10 minutes, preferably from 1 to 4 minutes. After this heating period the solution is allowed to cool to from 20°–40° C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. Thus, for example, if DNA polymerase is used as the agent for polymerization, the temperature is generally no greater than about 45° C. Preferably an amount of dimethylsulfoxide (DMSO) is present which is effective in detection of the signal or the temperature is 35°–40° C. Most preferably 5–10% by volume DMSO is present and the temperature is 35°–40° C. For certain applications, where the sequences to be amplified are over 110 base pair fragments, such as the HLA DQ-α or -β genes, an effective amount (e.g., 10% by volume) of DMSO is added to the amplification mixture, and the reaction is carried at 35°–40° C., to obtain detectable results or to enable cloning.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heatstable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional inducing agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a stepwise fashion where after each step new reagents are added, or simultaneously, where all reagents are added at the initial step, or partially step-wise and partially simultaneous, where fresh reagent is added after a given number of steps. If a method of strand separation, such as heat, is employed which will inactivate the agent for polymerization, as in the case of a heat-labile enzyme, then it is necessary to replenish the agent for polymerization after every strand separation step. The simultaneous method may be utilized when a number of purified components, including an enzymatic means such as helicase, is used for the strand separation step. In the simultaneous procedure, the reaction mixture may contain, in addition to the nucleic acid strand(s) containing the desired sequence, the strandseparating enzyme (e.g., helicase), an appropriate energy source for the strand-separating enzyme, such as rATP, the four nucleotides, the oligonucleotide primers in molar excess, and the inducing agent, e.g., Klenow fragment of E. coli DNA polymerase I. If heat is used for denaturation in a simultaneous process, a heat-stable inducing agent such as a thermostable polymerase may be employed which will operate at an elevated temperature, preferably 65°–90° C. depending on the inducing agent, at which temperature the nucleic acid will consist of single and double strands in equilibrium. For smaller lengths of nucleic acid, lower temperatures of about 50° C. may be employed. The upper temperature will depend on the temperature at which the enzyme will degrade or the temperature above which an insufficient level of primer hybridization will occur. Such a heat-stable enzyme is described, e.g., by A. S. Kaledin et al., *Biokhimiya*, 45, 644–651 (1980). Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

The process of the present invention may be conducted continuously. In one embodiment of an automated process, the reaction may be cycled through a denaturing region, a reagent addition region, and a reaction region. In another embodiment, the enzyme used for the synthesis of primer extension products can be immobilized in a column. The other reaction components can be continuously circulated by a pump through the column and a heating coil in series; thus the nucleic acids produced can be repeatedly denatured without inactivating the enzyme.

The present invention is demonstrated diagrammatically below where double-stranded DNA containing the desired sequence [S] comprised of complementary strands [S+] and [S−] is utilzied as the nucleic acid. During the first and each subsequent reaction cycle extension of each oligonucleotide primer on the original template will produce one new ssDNA molecule product of indefinite length which terminates with only one of the primers. These products, hereafter referred to as "long products," will accumulate in a linear fashion; taht is, the amount present after any number of cycles will be proportional to the number of cycles.

The long products thus produced will act as templates for one or the other of the oligonucleotide primers during subsequent cycles and will produce molecules of the desired sequence [S+] or [S−]. These molecules will also function as templates for one of the other of the oligonucleotide primers, producing further [S+] and [S−], and accumulation of [S] at an exponential rate relative to the number of cycles.

By-products formed by oligonucleotide hybridizations other than those intended are not self-catalytic (except in rare instances) and thus accumulates at a linear rate.

The specific sequence to be amplified, [S], can be depicted diagrammatically as:

```
[S+]    5' AAAAAAAAAAXXXXXXXXXXCCCCCCCCCC 3'
[S−]    3' TTTTTTTTTTYYYYYYYYYYGGGGGGGGGG 5'
```

The appropriate oligonucleotide primers would be:

Primer 1:    GGGGGGGGGG
Primer 2:    AAAAAAAAAA so that if DNA containing [S]

```
... zzzzzzzzzzzzzzzzAAAAAAAAAAXXXXXXXXXXCCCCCCCCCCzzzzzzzzzzzzzzzz ...
... zzzzzzzzzzzzzzzzTTTTTTTTTTYYYYYYYYYYGGGGGGGGGGzzzzzzzzzzzzzzzz ...
``` is separated into single strands and its single strands are hybridized to Primers 1 and 2, the following extension reactions can be catalyzed by DNA polymerase in the presence of the four deoxyribonucleoside triphosphates:

```
                                              3'            5'
          extends  ←─────────────────────── GGGGGGGGGG  Primer 1
... zzzzzzzzzzzzzzzzAAAAAAAAAAXXXXXXXXXXCCCCCCCCCCzzzzzzzzzzzzzzzz ...
original template strand+ original template strand+
... zzzzzzzzzzzzzzzzTTTTTTTTTTGGGGGGGGGGzzzzzzzzzzzzzzzz ...
     Primer 2    AAAAAAAAAA ───────────────→extends
                 5'          3'
```

On denaturation of the two duplexes formed, the products are:

```
3'                                                                5'
... zzzzzzzzzzzzzzzzTTTTTTTTTTYYYYYYYYYYGGGGGGGGGG
newly synthesized long product 1

5'                                                                3'
... zzzzzzzzzzzzzzzzAAAAAAAAAAXXXXXXXXXXCCCCCCCCCCzzzzzzzzzzzzzzzz ...
original template strand+

3'                                                                5'
... zzzzzzzzzzzzzzzzTTTTTTTTTTYYYYYYYYYYGGGGGGGGGGzzzzzzzzzzzzzzzz ...
original template strand−

5'                                                   3'
              AAAAAAAAAAXXXXXXXXXXCCCCCCCCCCzzzzzzzzzzzzzzzz ...
              newly synthesized long product 2
```

If these four strands are allowed to rehybridize with Primers 1 and 2 in the next cycle, -continued agent for polymerization will catalyze the following reactions:

```
     Primer 2      5'  AAAAAAAAAA ─────────────────▶ extends to here
... zzzzzzzzzzzzzzzzzzzzTTTTTTTTTTYYYYYYYYYYGGGGGGGGGG 5'
newly synthesized long product 1 extends ◀───────────────── GGGGGGGGGG 5' Primer 1
5'... zzzzzzzAAAAAAAAAAXXXXXXXXXXCCCCCCCCCCzzzzzzzzzzzzzzz ... 3'
original template strand⁺

Primer 2      5'  AAAAAAAAAA ─────────────────────▶extends
3'... zzzzzzzzzzzzzzzzzz TTTTTTTTTTYYYYYYYYYYGGGGGGGGGGzzzzzzzzz ... 5'
original template strand⁻ extends to here ◀───────────── GGGGGGGGGG 5' Primer 1
     5'   AAAAAAAAAAXXXXXXXXXXCCCCCCCCCCzzzzzzzzzzzzzzz ... 3'
         newly synthesized long product 2
```

If the strands of the above four duplexes are separated, the following strands are found:

```
          5' AAAAAAAAAAXXXXXXXXXXCCCCCCCCCC 3'
             newly synthesized [S⁺]

3'... zzzzzzzzzzzzzzzzzzzzTTTTTTTTTTYYYYYYYYYYGGGGGGGGGG 5'
first cycle synthesized long product 1

3'... zzzzzzzzzzzzzzzzzzzzTTTTTTTTTTYYYYYYYYYYGGGGGGGGGG 5'
newly synthesized long product 1

5'... zzzzzzzzzzzzzzzzzzzzAAAAAAAAAAXXXXXXXXXXCCCCCCCCCCzzzzzzzz ... 3'
original template strand⁺

5' AAAAAAAAAAXXXXXXXXXXCCCCCCCCCCzzzzzzzzzzzzzzz ... 3'
             newly synthesized long product 2

3'... zzzzzzzzzzzzzzzzTTTTTTTTTTYYYYYYYYYYGGGGGGGGGGzzzzzzzzzzzzzzz ... 5'
original template strand⁻

3' TTTTTTTTTTYYYYYYYYYYGGGGGGGGGG 5'
             newly synthesized [S⁻]

5' AAAAAAAAAAXXXXXXXXXXCCCCCCCCCCzzzzzzzzzzzzzzz ... 3'
             first cycle synthesized long product 2
```

It is seen that each strand which terminates with the oligonucleotide sequence of one primer and the complementary sequence of the other is the specific nucleic acid sequence [S] that is desired to be produced.

The steps of this process can be repeated indefinitely, being limited only by the amount of Primers 1 and 2, the agent for polymerization and nucleotides present. For detection, the number of cycles used is that required to produce a detectable signal, an amount which will depend, e.g., on the nature of the sample. For example, if the sample is pure or diluted, fewer cycles may be required than if it is a complex mixture. If the sample is human genomic DNA, preferably the number of cycles is from about 10–30.

The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

|  | Number of Double Strands After 0 to n Cycles | | |
|---|---|---|---|
| Cycle Number | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^n - n - 1)$ |

When a single-stranded nucleic acid is utilized as the template, only one long product is formed per cycle.

The method herein may be utilized to clone a particular nucleic acid sequence for insertion into a suitable expression vector. The vector may then be used to transform an appropriate host organism to produce the gene product of the sequence by standard methods of recombinant DNA technology.

Normally, such cloning would either involve direct ligation into a vector or the addition of oligonucleotide linkers followed by restriction enzyme cleavage. Both of these methods involve, however, the inefficient blunt-end ligation reaction. Also, neither technique would control for the orientation or multiplicity of insertion of the amplified product into the cloning vector.

The amplification process herein may yield a mixture of nucleic acids, resulting from the original template nucleic acid, the expected target amplified products, and various background non-target products. The amplified product can also be a mixture if the original template DNA contains multiple target sequences, such as in a heterozygous diploid genome or when there is a family of related genes.

The primers herein may be modified to assist the rapid and specific cloning of the mixture of the DNAs produced by the amplification reaction. In such modification the same or different restriction sites are incorporated at the 5' ends of the primers to result in restriction sites at the two ends of the amplified product. When cut with the appropriate enzymes, the amplified product can then be easily inserted into plasmid or viral vectors and cloned. This cloning allows the analysis or expression of individual amplified products, not a mixture.

Although the same restriction site an be used for both primers, the use of different sites allows the insertion of the product into the vector with a specific orientation and suppresses multiple insertions as well as insertions arising from amplifications based on only one of the two primers. The specific orientation is useful when cloning into single-strand sequencing vectors, when single-strand hybridization probes are used, or when the cloned product is being expressed.

One method to prepare the primers is to choose a primer sequence which differs minimally from the target sequence. Regions in which each of the primers is to be located are screened for homology to restriction sites appropriate to the desired vector. For example, the target sequence "CAGTATCCGA..." differs by only one base from one containing a BamHI site. A primer sequence is chosen to match the target exactly at its 3' end, and to contain the altered sequence and restriction site near its 5' end (for example, "CATgATCCGA...", where the lower case letter symbolizes a mismatch with the target sequence). This minimally altered sequence will not interfere with the ability of the primer to hybridize to the original target sequence and to initiate polymerization. After the first amplification cycle the primer is copied, becomes the target, and matches exactly with new primers. After the amplification process, the products are cleaved with the appropriate restriction enzymes, optionally separated from inhibitors of ligation such as the nucleotide triphosphates and salts by passing over a desalting column or molecular weight chromatography column, and inserted by ligation into a cloning vector such as bacteriophage M13. The gene may then be sequenced and/or expressed using well known techniques.

The second method for preparing the primers involves taking the 3' end of the primers from the target sequence and adding the desired restriction site(s) to the 5' end of the primer. For the above example, a HindIII site could be added to make the sequence "cgaagctt-CAGTATCCGA...", where lower case letters are as described above. The added bases would not contribute to the hybridization in the first cycle of amplification, but would match in subsequent cycles. The final amplified products are then cut with restriction enzyme(s) and cloned and expressed as described above. The gene being amplified may be, for example, human beta-hemaglobin or the human HLA DQ, DR or DP-$\alpha$ and -$\beta$ genes.

In addition, the process herein can be used for in vitro mutagenesis. The oligodeoxyribonucleotide primers need not be exactly complementary to the DNA sequence which is being amplified. It is only necessary that they be able to hybridize to the sequence sufficiently well to be extended by the polymerase enzyme or by whatever other inducing agent is employed. The product of a polymerase chain reaction wherein the primers employed are not exactly complementary to the original template will contain the sequence of the primer rather than the template, thereby introducing an in vitro mutation. In further cycles this mutation will be amplified with an undiminished efficiency because no further mispaired primings are required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers so as to induce further sequence changes. In this way a series of mutated sequences could gradually be produced wherein each new addition to the series could differ from the last in a minor way, but from the original DNA source sequence in an increasingly major way. In this manner changes could be made ultimately which were not feasible in a single step due to the inability of a very seriously mismatched primer to function.

In addition, the primer can contain as part of its sequence a non-complementary sequence provided that a sufficient amount of the primer contains a sequence which is complementary to the strand to be amplified. For example, a nucleotide sequence which is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Moreover, the process herein may be used to synthesize a nucleic acid fragment from an existing nucleic acid fragment which is shorter than its product (called the core segment) using certain primers the 3' ends of which are complemenary to or substantially complementary to the 3' ends of the single strands produced by separating the strands of the original shorter nucleic acid fragments, and the 5' ends of which primers contain sequence information to be appended to the core segment. This process comprises:

(a) treating the strands of said existing fragment with two oligonucleotide primers under conditions such that an extension product of each primer is synthesized which is complementary to each nucleic acid strand, wherein said primers are selected so as to be substantially complementary to the 3' end of each strand of said existing fragment such that the extension product synthesized from one primer, when it is separated from its complement, can serve as a template for synthesis of the extension product of the other primer, and wherein each primer contains, at its 5' end, a sequence of nucleotides which are not complementary to said existing fragent and which correspond to the two ends of the nucleic acid fragment being synthesized;

(b) separating the primer extension products from the templates on which they are synthesized to produce single-stranded molecules;

(c) treating the single-stranded molecules generated from step (b) with the primers of step (a) under conditions such that a primer extension product is synthesized using each of the single strands produced in step (b) as a template so as to produce two intermediate double-stranded nucleic acid molecules, into each of which has been incorporated the nucleotide sequence present in the 5' end of one of the oligonucleotide primers, and two full-length double-stranded nucleic acid molecules, into each of which has been incorporated the nucleotide sequence present in the 5' ends of both of the oligonucleotide primers;

(d) repeating steps (b) and (c) for a sufficient number of times to produce the full-length double-stranded molecule in an effective amount;

(e) treating the strands of the product of step (d) with two primers so as to lengthen the product of step (d) on both ends; and (f) repeating steps (a)–(d) using the product of step (d) as the core fragment and two oligonucleotide primers which are complementary or substantially complementary to the 3' ends of the single strands produced by separating the strands of the product of step (d).

Steps (b) and (c) are repeated as often as necessary, usually at least 5 times, to produce the required amount of the fulllength, double-stranded product to synthesize the final product (i.e., the effective amount). In addition, the core segment may be obtained as the product of a previous amplification cycle. The product produced in step (d) may be purified before a new cycle of extension and amplification, or used directly by employing the reaction mixture containing the product.

If the 3' ends of the primers are not exactly complementary to the 3' ends of the single strands of the original shorter nucleic acid, the core fragment of the product will not be exactly the same as the sequence information resident in the original shorter nucleic acid. Therefore, mutants of the original nucleic acid may be made by using primers which are substantially complementary at their 3' ends to the 3' ends of the single strands of the original shorter nucleic acid.

If restriction site linkers are incorporated into the primers, then the amplified double-stranded products can be digested with the appropriate restriction enzymes and ligated directly into an M13 vector for rapid cloning and sequencing. The M13 plaques containing the specific amplified target sequences can be identified by hybridizing plaque lift filters with a probe specific for the target sequence.

The method herein may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed but where rapid detection is desirable.

For purposes of this invention genetic diseases may include specific deletions and/or mutations in genomic DNA from any organism, such as, e.g., sickle cell anemia, cystic fibrosis, α-thalassemia, β-thalassemia, and the like. Sickle cell anemia can be readily detected via oligomer restriction analysis or a RFLP-like analysis following amplification of the appropriate DNA sequence by the present method. α-Thalassemia can be detected by the absence of a sequence, and β-thalassemia can be detected by the presence of a polymorphic restriction site closely linked to a mutation which causes the disease.

All of these genetic diseases may be detected by amplifying the appropriate sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of nonradioactive probes is facilitated by the high level of the amplified signal.

In another embodiment a small sample of DNA may be amplified to a convenient level and then a further cycle of extension reactions performed wherein nucleotide derivatives which are readily detectable (such as $^{32}$P-labeled or biotin labeled nucleoside triphosphates) are incorporated directly into the final DNA product, which may be analyzed by restriction and electrophoretic separation or any other appropriate method. An example of this technique in a model system is demonstrated in FIG. 5.

Figure 3:
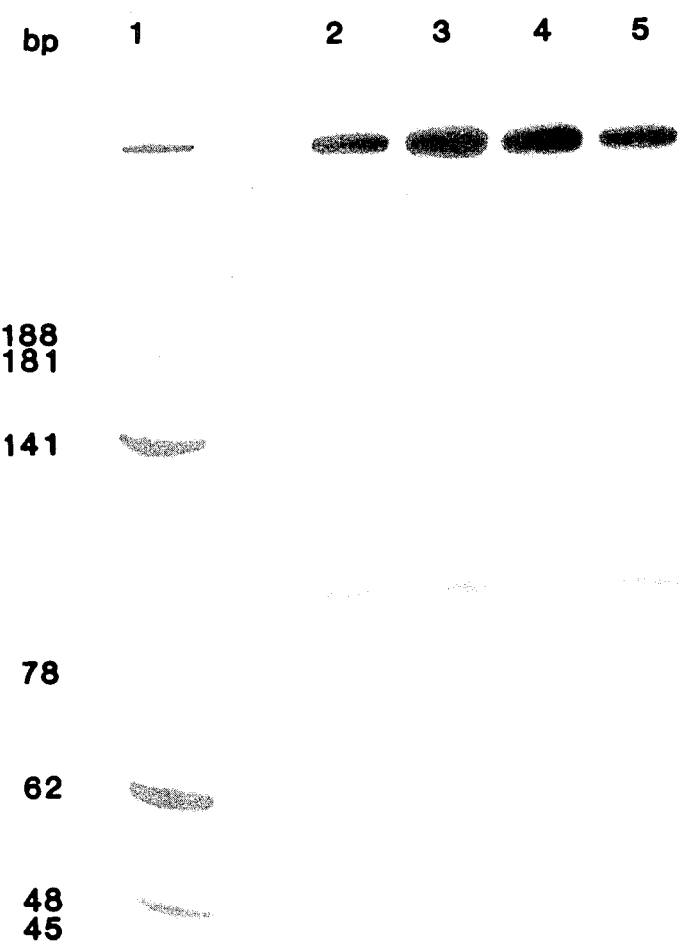
FIG. 3 illustrates a photograph of an ethidium bromidestained polyacrylamide gel demonstrating amplification of any of the specific target 94-mer sequence present in pBR328:HbA, a plasmid containing a 1.9 kb BamHI fragment of the sickel cell allele of β-globin (pBR328:HbS), pBR328:HbA where the sequence to be amplified is cleaved with MstII, and pBR328:HbS where the sequence to be amplified has been treated but not cleaved with MstII.

In a further embodiment, demonstrated in a model system in FIG. 3, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

Figure 7:
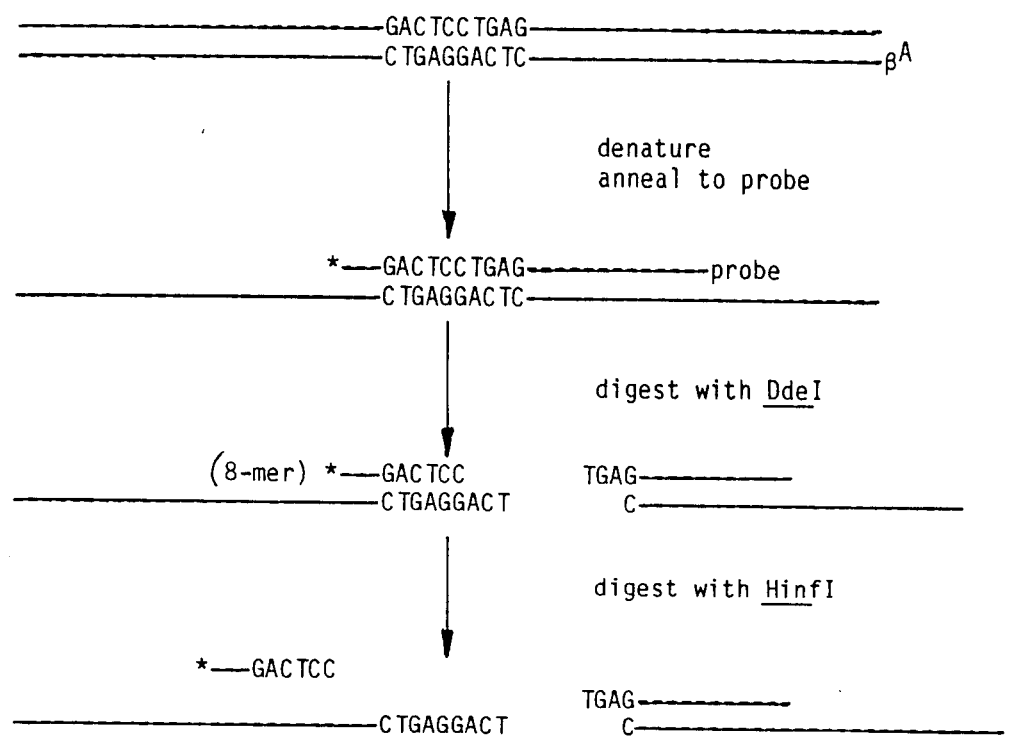
FIG. 7 illustrates the results of sequential digestion of normal β-globin using a 40-mer probe and DdeI followed by HinfI restriction enzymes.
Figure 8:
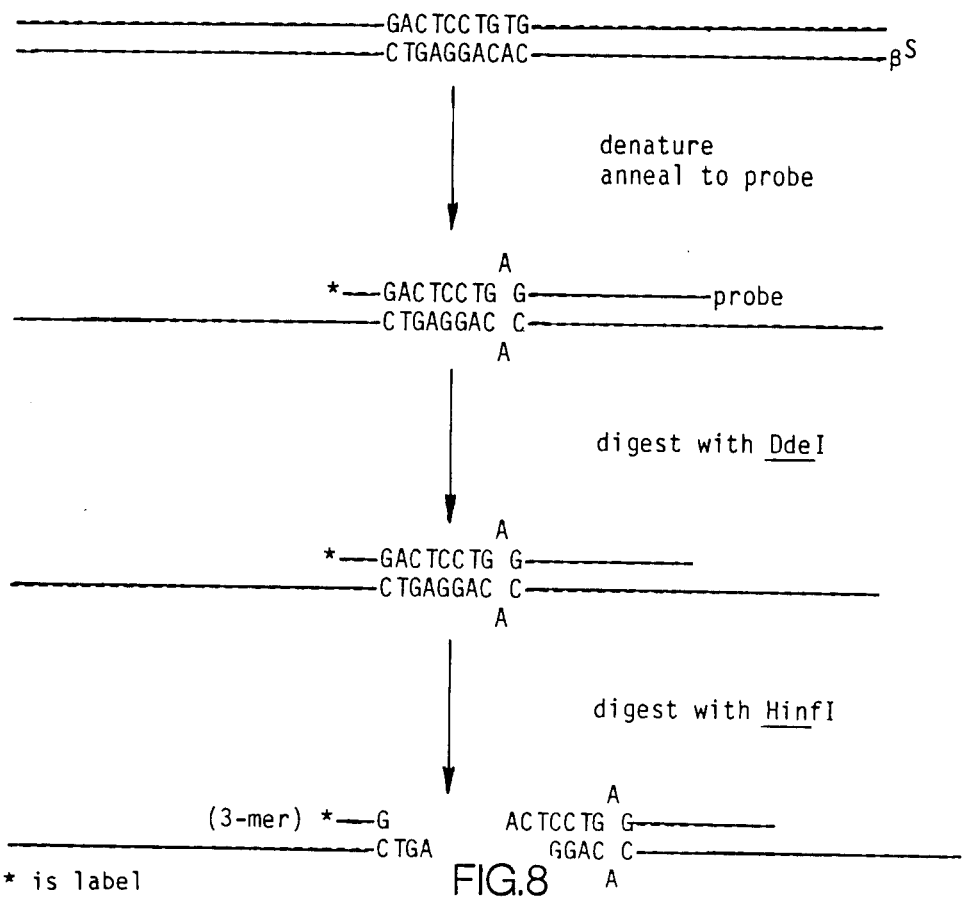
FIG. 8 illustrates the results of sequential digestion of sickel β-globin using the same 40-mer probe as in FIG. 7 and DdeI followed by HinfI restriction enzymes.

A practical application of this technique can be illustrated by its use in facilitating the detection of sickel cell anemia via the oligomer restriction technique described herein and in U.S. Pat. No. 4,683,194. Sickle cell anemia is a hemoglobin disease which is caused by a single base pair change in the sixth codon of the β-globin gene. FIG. 6 illustrates the sequences of normal and sickel cell β-globin genes in the region of their polymorphism, where the single bars mark the location of a DdeI site present only in the normal gene and where the double bars mark the location of a HinfI site which is nonpolymorphic and thus present in both the normal and sickel cell alleles. FIG. 7 illustrates the process of oligomer restriction of normal β-globin DNA using a probe spanning both restriction sites and labeled where the asterisk appears. (The probe is preferably labeled at the end which is fewer base pairs from the restriction site than the other end of the probe.) The DNA, amplified as provided herein, is denatured and annealed to the labeled probe. The amplification may be carried out at elevated temperatures (35°–40° C.) in the presence of dimethyl sulfoxide to minmize formation of secondary structure. The enzyme DdeI cleaves the DNA at the reformed DdeI site and generates a labeled octamer. Under the conditions used in the test the octamer is short enough to dissociate from the duplex. The subsequent addition of the enzyme HinfI has no effect on the now single-stranded octamer. Figure 8 illustrates the same process applied to the sickle cell allele of β-globin DNA. The enzyme DdeI cannot cleave the duplex formed by the amplfied DNA and the labeled probe because of the A—A base pair mismatch. The enzyme HinfI, however, does restrict the hybrid and a labeled trimer is produced. In practice the method can diagnose the DNA of an individual as being either homozygous for the wild type, homozygous for the sickel type or a heterozygous carrier of the sickle cell trait, since a specific signal is associated with the presence of either allele. Use of this above-described method to amplify the pertinent sequence allows for a rapid analysis of a single copy gene using a probe with only a single $^{32}P$ label.

Various infectious diseases can be diagnosed by the presence in clinical samples of specific DNA sequences characteristic of the causative microorganism. These include bacteria, such as Salmonella, Chlamydia, and Neisseria; viruses, such as the hepatitis viruses; and parasites, such as the Plasmodium responsible for malaria. U.S. Pat. No. 4,358,535 issued to Falkow describes the use of specific DNA hybridization probes for the diagnosis of infectious diseases. A problem inherent in the Falkow procedure is that a relatively small number of pathogenic organisms may be present in a clinical sample from an infected patient and the DNA extracted from these may constitute only a very small fraction of the total DNA in the sample. Specific amplification of suspected sequences prior to immobilization and hybridization detection of the DNA samples could greatly improve the sensitivity and specificity of these procedures.

Routine clinical use of DNA probes for the diagnosis of infectious disesases would be simplified considerably if nonradioactively, labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow and Ward procedures useful in a routine clincal setting.

In addition, the probe may be a biotinylated probe in which the biotin is attached to a spacer arm of the formula:

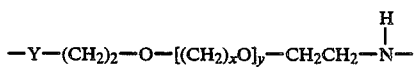

where Y is O, NH or N—CHO, x is a number from 1 to 4, and y is a number from 2 to 4. The spacer arm is in turn attached to a psoralen moiety of the formula:

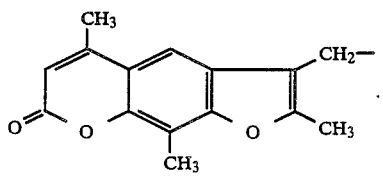

The psoralen moiety intercalates into and crosslinks a "gapped circle" probe as described by Courage-Tebbe et al., Biochim, Biophys. Acta, 697 (1982) 1–5, wherein the single-stranded hybridization region of the gapped circle spans the region contained in the primers. The details of this biotinylation and dot blot procedure are described more fully in U.S. Pat. Nos. 4,582,789 and 4,617,261, the disclosures of which are incorporated herein by reference.

The amplification process can also be utilized to produce sufficient quantities of DNA from a single copy human gene such that detection by a simple non-specific DNA stain such as ethidium bromide can be employed so as to make a DNA diagnosis directly.

In addition to detecting infectious diseases and pathological abnormalities in the genome of organisms, the process herein can also be used to detect DNA polymorphism which may not be associated with any pathological state.

The following examples are offered by way of illustration and are not intended to limit the invention in any manner. In these examples all percentages are by weight if for solids and by volume if for liquids, and all temperatures are in degrees Celsius unless otherwise noted.

EXAMPLE 1

A 25 base pair sequence having the nucleotide sequence

5' CCTCGGCACCGTCACCCTGGATGCT 3'

3' GGAGCCGTGGCAGTGGGACCTACGA 5' contained on a 47 base pair FokI restriction fragment of pBr322 obtainable from ATCC was prepared as follows. A FokI digest of pBR322 containing the 47-bp fragment was produced by digesting pBR322 with FokI in accordance with the conditions suggested by the supplier, New England Biolabs Inc. The primers which were utilized were 5' d(CCTCGGCACCG) 3' and 5' d(AGCATCCAGGGTG) 3', and were prepared using conventional techniques. The following ingredients were added to 33 µl of buffer which consisted of 25 mM potassium phosphate, 10 mM magnesium chloride and 100 mM sodium chloride at pH 7.5: 2433 pmoles of each of the primers described above, 2.4 pmoles of the FokI digest of pBR322, 12 nmoles of dATP, 22 nmoles of dCTP, 19 nmoles of dGTP and 10 nmoles of TTP.

The mixture was heated to 85° C. for five minutes and allowed to cool to ambient temperature. Five units of the Klenow fragment of E. coli DNA polymerase I were added and the temperature was maintained for 15 minutes. After that time, the mixture was again heated to 85° C. for five minutes and allowed to cool. Five units of the Klenow fragment were again added and the reaction was carried out for 15 minutes. The heating, cooling and synthesis steps were repeated eleven more times.

After the final repetition, a 5 µl aliquot was removed from the reaction mixture. This was heated to 85° C. for three minutes and allowed to cool to ambient temperature. 12.5 pmoles of α-$P^{32}$ -deoxycytidine triposphate and 5 units of Klenow fragment were added and the reaction was allowed to proceed for 15 minutes. The labeled products were examined by polyacrylamide gel electrophoresis. The FokI digest was labeled in a similar fashion and served as a control and molecular weight markers. The only heavily labeled band visible after the 13 cycles was the intended 25 base pair sequence.

EXAMPLE 2

The desired sequence to be amplified was a 94 base pair sequence contained within the human beta-globin gene and spanning the MstII site involved in sickle cell anemia. The sequence has the nucleotide sequence shown in FIG. 1.

I. Synthesis of Primers

The following two oligodeoxyribonucleotide primers were prepared by the method described below:

5' CACAGGGCAGTAACG 3' Primer A and

5' TTTGCTTCTGACACA 3' Primer B

Automated Synthesis Procedures: The diethylphosphoramidites, synthesized according to Beaucage and Caruthers (*Tetrahedron Letters* (1981) 22:1859-1862), were sequentially condensed to a nucleoside derivatized controlled pore glass support using a Biosearch SAM-1. The procedure included detritylation with trichloracetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxyribonucleotide was brought to 55° C. for five hours. Ammonia was removed and the residue was applied to a preparative polyacrylamide ge. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7-13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

Characterization of Oligodeoxyribonucleotides: Test aliquots of the purified oligonucleotides were $^{32}$P labeled with polynucleotide kinase and $\gamma$-$^{32}$P-ATP. The labeled compounds were examined by autoradiography of 14-20% polyacrylamide gels after electrophoreis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Source of DNA

A. Extraction of Whole Human Wild-Type DNA

Human genomic DNA homozygous for normal $\beta$-globin was extracted from the cell line Molt4 (obtained from Human Genetic Mutant Cell Repository and identified as GM2219c) using the technique described by Stetler et al., *Proc. Nat. Acad. Sci. USA* (1982), 79:5966-5970.

B. Construction of Cloned Globin Genes

A 1.9 kb BamHI fragment of the normal $\beta$-globin gene was isolated from the cosmid pFC11 and inserted into the BamHI set of pBR328 (Soberon, et al., Gene (1980) 9:287-305). This fragment, which encompasses the region that hybridizes to the synthetic 40-mer probe, includes the first and second exons, first intron, and 5' flanking sequences of the gene (Lawn et al., Cell (1978), 15:1157-1174). This clone was designated pBR328:HbA and deposited under ATCC No. 39,698 on May 25, 1984.

The corresponding 1.9 kb BamHI fragment of the sickle cell allele of $\beta$-globin was isolated from the cosmid pFC12 and cloned as described above. This clone was designated pBR328:HbS and deposited under ATCC No. 39,699 on May 25, 1984.

Each recombinant plasmid was transformed into and propagated in *E. coli* MM294 (ATCC No. 39,607).

C. Digestion of Cloned Globin Genes with MstII

A total of 100 $\mu$g each of pBR328:HbA and pBR328:HbS were individually digested with 20 units of MstII (New England Biolabs) for 16 hours at 37° C. in 200 $\mu$l of 150 mM NaCl, 12 mM Tris HCl (pH 7.5), 12 mM MgCl$_2$, 1 mM dithiothreitol (DTT), and 100 $\mu$g/ml bovine serum albumin (BSA). The products are designated pBR328:HbA/MstII and pBR328:HbS/MstII, respectively.

III. Polymerase Chain Reaction

To 100 $\mu$l of buffer consisting of 60 mM sodium acetate, 30 mM tris acetate and 10 mM magnesium acetate at pH 8.0 was added 2 $\mu$l of a solution containing 100 picomoles of Primer A (of the sequence d(CACAGG-GCACTAACG)), 100 picomoles of Primer B (of the sequence d(TTTGCTTCTGACACA)) and 1000 picomoles each of dATP, dCTP, dGTP and TIP. In addition, one of the following sources of DNA described above was added:

10 $\mu$g whole human wild-type DNA (Reaction I)
0.1 picomole pBR328:HbA (Reaction II)
0.1 picomole pBR328:HbS (Reaction III)
0.1 picomole pBR328:HbA/MstII (Reaction IV)
0.1 picomole pBR328:HbS/MstII (Reaction V)
No target DNA (Reaction VI)

Each resulting solution was heated to 100° C. for four minutes and allowed to cool to room temperature for two minutes, whereupon 1 $\mu$l containing four units of Klenow fragment of *E. coli* DNA polymerase was added. Each reaction was allowed to proceed for 10 minutes, after which the cycle of adding the primers, nucleotides and DNA, heating, cooling, adding polymerase, and reacting was repeated nineteen times for Reaction I and four times for Reactions II-VI.

Four microliter aliquots of Reactions I and II removed before the first cycle and after the last cycle of each reaction were applied to a 12% polyacrylamide gel 0.089 M in Tris-borate buffer at pH 8.3 and 2.5 mM in EDTA. The gel was electrophoresed at 25 volts/cm for four hours, transferred to a nylon membrane serving as solid phase support and probed with a 5'-$^{32}$P-labeled 40 bp synthetic fragment, prepared by standard techniques, of the sequence 5'd(TCCTGAGGAGAAGTCTGCCGT-
TACTGCCCTGTGGGGCAAG)3' in 30% formamide, 3 x SSPE, 5 x Denhardt's, 5% sodium dodecyl sulfate at pH 7.4. FIG. 2 is an autoradiograph of the probed nylon membrane for Reactions I and II. Lane 1 is 0.1 picomole of a 58-bp synthetic fragment control one strand of which is complementary to the above probe. Lane 2 is 4 μl of Reaction I prior to the first amplification cycle. Lane 3 is 4 μl of Reaction I after the 20th amplification cycle. Lane 4 is 4 μl of Reaction II after five amplification cycles. Lane 5 is a molecular weight standard consisting of FokI (New England Biolabs) digest of pBR322 (New England Biolabs) labeled with alpha-$^{32}$P-dNTPs and polymerase. Lane 3 shows that after twenty cycles the reaction mixture I contained a large amount of the specific sequence of the proper molecular weight and no other detectable products. Reaction mixture II after five cycles also contained this product, as well as the starting nucleic acid and other products, as shown by Lane 4.

To 5.0 μl aliquots of Reactions II-VI after the fourth cycle were added 5 pmoles of each primer described above. The solutions were heated to 100° C. for four minutes and allowed to equilibrate to room temperature. Three pmoles each of alpha-$^{32}$P-dATP, alpha-$^{32}$P-cCTP, alpha-$^{32}$P-dGTP and alpha-$^{32}$P-TTP and four units of Klenow fragment were added. The reaction, in a final volume of 10 μl and at the salt concentrations given above, was allowed to proceed for 10 minutes. The polymerase activity was terminated by heating for 20 minutes at 60° C. Four μl aliquots of Reactions II-VI were loaded onto a 12% polyacrylamide gel 0.089 M in Tris-borate buffer at pH 8.3 and 2.5 mM in EDTA. The gel was electrophoresed at 25 volts/cm for four hours after which autoradiography was performed.

FIG. 3 is an autoradiograph of the electrophoresis. Lane 1 is a molecular weight standard, Lane 2 is Reaction II, Lane 3 is Reaction III, Lane 4 is Reaction IV and Lane 5 is Reaction V. Another lane for Reaction VI with no DNA as control had no images in any of the lanes. It can be seen from the figure that the 94-bp fragment predicted from the target DNA was present only where intact β-globin DNA sequences were available for amplification, i.e., pBR328:HbA (Lane 2), pBR328:HbS (Lane 3) and pBR328:HbS/MstII (Lane 5). MstII digestion cuts pBR328:HbA in the 94-mer sequence rendering it incapable of being amplified, and the 94-mer band does not appear in Lane 4. In contrast, the 94-mer sequence in pBR328:HbS does not cut when the plasmid is digested with MstII and thus is available for amplification as shown in Lane 5.

FIG. 4 illustrates the chain reaction for three cycles in amplifying the 94-bp sequence. PC01 and PC02 are Primers A and B. The numbers on the right indicate the cycles, whereas the mumbers on the left indicate the cycle number in which a particular molecule was produced.

EXAMPLE 3

This example illustrates amplification of a 110 bp sequence spanning the allelic MstII site in the human homoglobin gene.

A total of 1.0 microgram whole human DNA, 100 picomoles d(ACACAACTGTGTTCACTAGC) and 100 picomoles d(CAACTTCATCCACGTTCACC), the primers having been prepared by the technique of Example 2, were dissolved in 100 μl of a solution which was:

1.5 mM in each of the four deoxyribonucleoside triphosphates
30 mM in Tric acetate buffer at pH 7.9
60 mM in sodium acetate
10 mM in magnesium acetate
0.25 mM in dithiothreitol The solution was heated to 100° C. for one minute and brought rapidly to 25° C. for one minute, after which was added 2.5 units Klenow fragment of DNA polymerase. The polymerase reaction was allowed to proceed for two minutes at 25° C., after which the cycle of heating, cooling, adding Klenow, and reacting was repeated as often as desired.

With a 70% efficiency at each cycle, 15 cycles resulted in the synthesis of 1.4 femtomoles of the desired 110 bp fragment of the β-globin gene.

EXAMPLE 4

This example illustrates amplification of a 240 bp sequence spanning the allelic MstII site in the human hemoglobin gene. This sequence contains NcoI, HinfI and MstII restriction sites.

Figure 5:
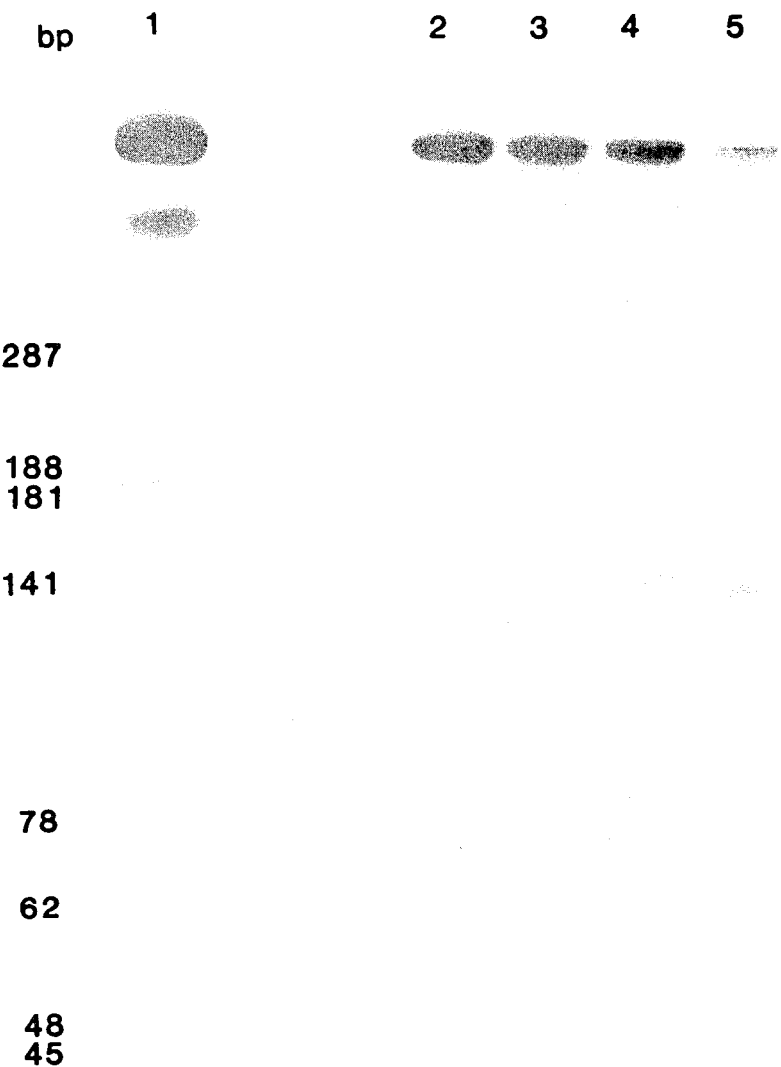
FIG. 5 represents a photograph of an ethidium bromidestained polyacrylamide gel demonstrating amplification after four cycles of a 240-mer sequence in pBR328:HbA, where the aliquots are digested with NcoI (Lane 3), MstII (Lane 4) or HinfI (Lane 5). Lane 1 is the molecular weight standard and Lane 2 contains the intact 240-bp product.

To 100 μl of a mixture of 60 mM sodium acetate, 30 mM Tris acetate and 10 mM magnesium acetate at pH 8.0 containing 0.1 pmole pBR328:HbA was added 2 μl of Solution A containing:
  100 pmoles d(GGTTGGCCAATCTACTCCCAGG) primer
  100 pmoles d(TAACCTTGATACCAACCTGCCC) primer
  1000 pmoles each of dATP, dCTP, dGTP and TTP The two primers were prepared by the technique described in Example 2. The solution was heated to 100° C. for four minutes and allowed to cool in ambient air for two minutes, after which added 1 μl containing four units Klenow fragment of E. coli DNA polymerase. The reaction was allowed to proceed for 10 minutes after which the cycle of solution A addition, heating, cooling, adding polymerase, and reacting was repeated three times. To a 5.0 μl aliquot of the reactions was added 5 picomoles of each oligonucleotide primer described above. The solution was heated to 100° C. for four minutes and allowed to come to ambient temperature, after which 3 picomoles each of the alpha-$^{32}$P-labeled deoxyribonucleoside triphosphates and 4 units Klenow fragment were added. The reaction, in a final volume of 10 μl and at the salt concentrations given above, was allowed to proceed for 10 minutes. The polymerase activity was terminated by heating for 20 minutes at 60° C. Two μl aliquots were digested with NcoI, MstII, or HinfI and loaded onto a 12% polyacrylamide gel 0.089 M in Tris-borate buffer at pH 8.3 and 2.5 mM in EDTA. The gel was electrophoresed at 25 volts/cm for four hours and autoradiography was performed. FIG. 5 illustrates the autoradiograph of the electrophoresis, where Lane 1 is the molecular weight standard, Lane 2 is without digestion with enzyme (240 bp intact), Lane 3 is digestion with NcoI (131 and 109 bp), Lane 4 is digestion with MstII (149 and 91 bp), and Lane 5 is digestion with HinfI (144 and 96 bp). The autoradiograph is consistent with the amplification of the 240 bp sequence.

EXAMPLE 5

This example illustrates use of the process herein to detect sickle cell anemia by sequential digestion. Synthesis and Phosphorylation of Oligodeoxyribonucleotides A labeled DNA probe, RS06, of the sequence:
  5′ *CTGACTCCTGAGGAGAAGTCTGCCGTTACTGCCCTGTGGG 3′ where * indicates the label, and an unlabeled blocking oligomer, RS10, of the sequence:

3' GACAGAGGTCACCTCTTCAGACG-GCAATGACGGGACACCC 5' which has three base pair mismatches with RS06 were synthesized according to the procedures provided in Example 2(I). The probe RS06 was labeled by contacting five pmole thereof with 4 units of T4 polynucleotide kinase (New England Biolabs) and 50 pmole $\gamma^{32}$P-ATP (New England Nuclear, about 7200 Ci/mmole) in a 40 µl reaction volume containing 70 mM Tris buffer (ph 7.6), 10 mM MgCl$_2$, 1.5 mM spermine, and 2.5 mM dithiothreitol for 90 minutes at 37° C. The total volume was then adjusted to 100 µl with 25 mM EDTA and purified according to the procedure of Maniatis et al., Molecular Cloning: A Laboratory Manual (New York: Cold Spring Harbor Laboratory, 1982), pp. 464–465, over a 1 ml Bio Gel P-4 spin dialysis column from Bio-Rad equilibrated with Tris-EDTA (TE) buffer (10 mM Tris buffer, 0.1 mM EDTA, pH 8.0). The labeled probe was further purified by electrophoresis on a 18% polyacrylamide gel (19:1 acrylamide:BIS, BioRad) in Tris-boric acid-EDTA, (TBE) buffer (89 mM Tris, 89 mM boric acid, 2.5 mM EDTA, pH 8.3) for 500 vhr. After localization by autoradiography, the portion of the gel containing the labeled probe was excised, crushed and eluted into 0.2 ml TE buffer overnight at 4° C. TCA precipitation of the reaction product indicated that the specific activity was 4.9 Ci/mmole and the final concentration was 20 pmole/ml.

The unlabeled RS10 blocking oligomer was used at a concentration of 200 pmole/ml.

Isolation of Human Genomic DNA from Cell Lines

High molecular weight genomic DNA was isolated from the lymphoid cell lines Molt4, SC-1 and GM2064 using essentially the method of Stetler et al., Proc. Natl. Acad. Sci. USA (1982), 79, 5966–5970 (for Molt4) and Maniatis et al, Molecular Cloning: A Laboratory Manual (New York: Cold Spring Harbor Laboratory, 1982), pp. 280–281.

Molt4 (Human Mutant Cell Repository, GM2219C) is a T cell line homozygous for normal $\beta$-globin, and SC-1, deposited with ATCC on Mar. 19, 1985, is an EBV-transformed B cell line homozygous for the sickle cell allele. GM2064 (Human Mutant Cell Repository, GM2064) was originally isolated from an individual homozygous for hereditary persistance of fetal hemoglobin (HPFH) and contains no beta- or deltaglobin gene sequences. All cell lines were maintained in RPMI-1640 with 10% fetal calf serum.

Isolation of Human Genomic DNA from Clinical Blood Samples

A clinical blood sample designated CH12 from a known sickle cell carrier (AS) was obtained from Dr. Bertram Lubin of Children's Hospital in Oakland, California. Genomic DNA was prepared from the buffy coat fraction, which is composed primarily of peripheral blood lymphocytes, using a modification of the procedure described by Nunberg et al., Proc. Nat. Acad. Sci. USA, 75, 5553–5556 (1978).

The cells were resuspended in 5 ml Tris-EDTA-NaCl (TEN) buffer (10 mM Tris buffer pH 8, 1 mM EDTA, 10 mM NaCl) and adjusted to 0.2 mg/ml proteinase K, 0.5% SDS, and incubated overnight at 37° C. Sodium perchlorate was then added to 0.7 M and the lysate was gently shaken for 1–2 hours at room temperature. The lysate was extracted with 30 ml phenol/chloroform (1:1), then with 30 ml chloroform, and followed by ethanol precipitation of the nucleic acids. The pellet was resuspended in 2 ml of TE buffer and RNase A added to 0.005 mg/ml. After digestion for one hour at 37° C., the DNA was extracted once each with equal volumes of phenol, phenol/chloroform, and chloroform, and ethanol precipitated. The DNA was resuspended in 0.5 ml TE buffer and the concentration was determined by absorbance at 260 nm.

Polymerase Chain Reaction to Amplify Selectively $\beta$-Globin Sequences

Two micrograms of genomic DNA was amplified in an initial 100 µl reaction volume containing 10 mM Tris Buffer (pH 7.5), 50 mM NaCl, 10 mM MgCl$_2$, 150 pmole of Primer A of the sequence d(CACAGG-GCACTAACG), and 150 pmole of Primer B of the sequence d(CTTTGCTTCTGACACA) and overlayed with about 100 µl mineral oil to prevent evaporation.

Each DNA sample underwent 15 cycles of amplification where one cycle is composed of three steps:

1. Denature in a heat block set at 95° C. for two minutes.

2. Transfer immediately to a heat block set at 30° C. for two minutes to allow primers and genomic DNA to anneal.

3. Add 2 µl of a solution containing 5 units of the Klenow fragment of E. coli DNA polymerase I (New England Biolabs), 1 nmole each of dATP, dCTP, dGTP and TTP, in a buffer composed of 10 mM Tris (pH 7.5), 50 mM NaCl, 10 mM MgCl$_2$, and 4 mM dithiothreitol. This extension reaction was allowed to proceed for 10 minutes at 30° C.

After the final cycle, the reaction was terminated by heating at 95° C. for two minutes. The mineral oil was extracted with 0.2 ml of chloroform and discarded. The final reaction volume was 130 µl.

Hybridization/Digestion of Amplified Genomic DNA with Probes and DdeI/HinfI

Forty-five microliters of the amplifier genomic DNA was ethanol precipitated and resuspended in an equal volume of TE buffer. Ten microliters (containing the pre-amplification equivalent of 154 ng of genomic DNA) was dispensed into a 1.5 ml Microfuge tube and 20 µl of TE buffer to a final volume of 30 µl. The sample was overlayed with mineral oil and denatured at 95° C. for 10 minutes. Ten microliters of 0.6 M NaCl containing 0.02 pmole of labeled RS06 probe was added to the tube, mixed gently, and immediately transferred to a 56° C. heat block for one hour. Four microliters of unlabeled RS10 blocking oligomer (0.8 pmole) was added and the hybridization continued for an additional 10 minutes at the same temperature. Five microliters of 60 mM MgCl$_2$/0.1% BSA and 1 µl of DdeI (10 units, New England Biolabs) were added and the reannealed DNA was digested for 30 minutes at 56° C. One microliter of HinfI (10 units, New England Biolabs) was then added and incubated for another 30 minutes. The reaction was stopped by the addition of 4 µl 75 nM EDTA and 6 µl tracking dye to a final volume of 61 µl.

The mineral oil was extracted with 0.2 ml chloroform, and 18 µl of the reaction mixture (45 ng genomic DNA) was loaded onto a 30% polyacrylamide mini-gel (19:1, Bio-Rad) in a Hoeffer SE200 apparatus. The gel was electrophoresed at approximately 300 volts for one hour until the bromphenol blue dye front migrated to 3.0 cm off-origin. The top 1.5 cm of the gel was removed and the remaining gel was exposed for four days with one intensification screen at −70° C. Discussion of Photograph (FIG. 9)

Each lane contains 45 ng of amplified genomic DNA. Lane A contains Molt4 DNA; Lane B, CH12; Lane C, SC-1; and Lane D, GM2064. Molt4 represents the genotype of a normal individual with two copies of the $\beta^A$ gene per cell (AA), CH12 is a clinical sample from a sickle cell carrier with one $\beta^A$ and one $\beta^S$ gene per cell (AS), and SC-1 represents the genotype of a sickle cell individual with two copies of the $\beta^S$ gene cell (SS). GM2064, which contains no beta- or delta-globin sequences, is present as a negative control.

As seen in the photograph, the DdeI-cleaved, $\beta^A$-specific octamer is present only in those DNA's containing the $\beta^A$ gene (Lanes A and B), and the HinfI-cleaved, $\beta^S$-specific trimer is present only in those DNA's containing the $\beta^S$ gene (Lanes B and C). The presence of both trimer and octamer (Lane B) is diagnostic for a sickle cell carrier and is distinguishable from a normal individual (Lane A) with only octamer and a sickle cell afflicted individual (Lane C) with only trimer.

As a comparison, repeating the experiment described above using non-amplified genomic DNA revealed that the amplification increased the sensitivity of detection by at least 1000 fold.

EXAMPLE 6

This example illustrates direct detection of a totally unpurified single copy gene in whole human DNA on gels without the need for a labeled probe.

Using the technique described in Example 3, a 110-bp fragment from a sequence in the first exon of the beta-globin gene was amplified from 10 micrograms of whole human DNA after 20 cycles. This 110-bp fragment produced after 20 cycles was easily visualized on gels stained with ethidium bromide.

The sequence was not amplified when it was first cut with the restriction enzyme DdeI unless, as in the beta-globin S allele, the sequence does not contain the restriction site recognized by the enzyme.

EXAMPLE 7

A. A total of 100 fmoles pBR328 containing a 1.9 kb insert from the human beta-globin A allele, 50 nmoles each alpha-32P-dNTP at 500 Ci/mole, and 1 nmole of each of the primers used in Example 3 were dissolved in a solution containing 100 μl 30 mM Tris-acetate at pH 7.9, 60 mM sodium acetate, 100 mM dithiothreitol, and 10 mM magnesium acetate. This solution was brought to 100° C. for two minutes and cooled to 25° C. for one minute. A total of 1 μl containing 4.5 units Klenow fregment of E. coli DNA polymerase I and 0.09 units inorganic pyrophosphatase was added to prevent the possible build-up of pyrophosphate in the reaction mixture and the reaction was allowed to proceed for two minutes at 25° C., after which the cycle of heating, cooling, adding enzyme, and reacting was repeated nine times. Ten-μl aliquots were removed and added to 1 μl 600 mM EDTA after each synthesis cycle. Each was analyzed on a 14% polyacrylamide gel in 90 mM Tris-borate and 2.5 mM EDTA at pH 8.3 and 24 volts/cm for 2.5 hours. The completed gel was soaked for 20 minutes in the same buffer with the addition of 0.5 μg/ml ethidium bromide, washed with the original buffer, and photographed in UV light using a red filter.

The 110-bp fragment produced was excised from the gel under ultraviolet light and the incorporated $^{32}$P counted by Cerenkov radiation. An attempt to fit the data to an equation of the form: pmoles/10 μl =0.01 $[(1+y)^N-yN-1]$, where N represents the number of cycles and the y fractional yield per cycle, was optimal with y=0.619. This indicates that a significant amplification is occurring.

B. The above experiment was repeated except that 100 nmoles of each dNTP was added to a 100 μl reaction, no radiolabel was employed, and aliquots were not removed at each cycle. After 10 cycles the reaction was terminated by boiling for two minutes and rehybridization was performed at 57° C. for one hour. The sequence of the 110-bp product was confirmed by subjecting 8 μl aliquots to restriction analysis by addition of 1 μl bovine serum albumin (25 mg/ml) and 1 μl of the appropriate restriction enzyme (HinfI, MnlI, MstII, NcoI) and by reaction at 37° C. for 15 hours. PAGE was peformed as described above.

EXAMPLE 8

This example illustrates the use of different primers to amplify various fragments of pBR328 and 322.

A. The experiment described in Example 7A was repeated except using the following primers: d(TTTGCTTCTGACACAACTGTGTTCAC-TAGC) and d(GCCTCACCACCAACTTCATC-CACGTTCACC) to produce a 130-bp fragment of pBR328.

B. The experiment described in Example 7A was repeated except using the following primers: d(GGTTGGCCAATCTACTCCCAGG) and d(TGGTCTCCTTAAACCTGTCTTG) to produce a 262-bp fragment of pBR328. The reaction time was 20 minutes per cycle.

C. The experiment described in Example 8B was repeated except that 100 fmoles of an MstII digest of pBR328 containing a 1.9 kb insert from the human beta-globin S allele was used as initial template. This plasmid was cleaved several times by MstII but not inside the sequence to be amplified. In addition, the primers employed were as follows:

d(GGTTGGCCAATCTACTCCCAGG) and d(TAACCTTGATACCAACCTGCCC)

to produce a 240-bp fragment.

D. The experiment described in Example 7B was repeated except that 100 fmoles of an NruI digest of pBR322 was used as template, 200 nmoles of each dNTP were used in the 100 μl reaction, and the primers were:

d(TAGGCGTATCACGAGGCCCT) and d(CTTCCCCATCGGTGATGTCG)

to produce a 500-bp fragment from pBR322. Reaction times were 20 minutes per cycle at 37° C. Final rehybridization was 15 hours at 57° C. Electrophoresis was on a 4% agarose gel.

EXAMPLE 9

This example illustrates the invention process wherein an in vitro mutation is introduced into the amplified segment.

A. A total of 100 fmole of pBR322 linearized with NruI, 1 nmole each of the primers:

d(CGCATTAAAGCTTATCGATG) and d(TAGGCGTATCACGAGGCCCT)

designed to produce a 75-bp fragment, 100 nmole each dNTP, in 100 μl 40 mM Tris at pH 8, 20 mM in MgCl2, 5 mM in dithiothreitol, and 5 mg/ml bovine serum albumin were combined. The mixture was brought to 100° C. for one minute, cooled for 0.5 minutes in a water bath at 23° C., whereupon 4.5 units Klenow fragment and 0.09 units inorganic pyrophosphatase were added, and a reaction was allowed to proceed for three minutes. The cycle of heating, cooling, adding enzymes, and reacting was repeated nine times. The tenth reaction cycle was terminated by freezing and an 8-μl aliquot of the reaction mixture was applied to a 4% agarose gel visualized with ethidium bromide.

B. The experiment described in Example 9A was repeated except that the oligonucleotide primers employed were:

d(CGCATTAAAGCTTATCGATG) and d(AATTAATACGACTCACTATAGG-
GAGATAGGCGTATCACGAGGCCCT).

These primers are designed to produce a 101-bp fragment, 26 nucleotides of which (in the second listed primer) are not present in pBR322. These nucleotides represent the sequence of the T7 promoter, which was appended to the 75-bp sequence from pBR322 by using the primer with 20 complementary bases and a 26-base 5' extension. The procedure required less than two hours and produced two picomoles of the relatively pure 101-bp fragment from 100 fmoles of pBR322.

The T7 promoter can be used to initiate RNA transcription. T7 polymerase may be added to the 101-bp fragment to produce single-stranded RNA.

C. The experiment described in Example 8D was repeated except that the oligonucleotide primers employed were as follows:

d(TAGGCGTATCACGAGGCCCT) and d(CCAGCAAGACGTAGCCCAGC)

to produce a 1000-bp frament from pBR322.

D. The experiment described in Example 9C was repeated except that the oligonucleotide primers employed were as follows:

d(TAGGCGTATCACGAGGCCCT) and d(AATTAATACGACTCACTATAGG-
GAGATAGGCGTATCACGAGGCCCT)

so as to produce a 1026-bp fragment, 26 nucleotides of which (in the second listed primer) are not present in pBR322 and represent the T7 promoter described above. The promoter has been inserted adjacent to a 1000-bp fragment from pBR322.

The results indicate that a primer which is not a perfect match to the template sequence but which is nonetheless able to hybridize sufficiently to be enzymatically extended produces a long product which contains the sequence of the primer rather than the corresponding sequence of the original template. The long product serves as a template for the second primer to introduce an in vitro mutation. In further cycles this mutation is amplified with an undiminished efficiency, because no further mispaired primings are required. In this case, a primer which carries a non-complementary extension on its 5' end was used to insert a new sequence in the product adjacent to the template sequence being copied.

EXAMPLE 10

This example illustrates employing nested sets of primers to decrease the background in the amplification of single copy genes.

Whole human DNA homozygous for the wild-type β-globin allele was subjected to twenty cycles of amplification as follows: A total of 10 μg DNA, 200 picomoles each of the primers:

d(ACACAACTGTGTTCACTAGC) and d(CAACTTCATCCACGTTCACC)

and 100 nanomoles each dNTP in 100 μl of 30 mM Tris-acetate pH 7.9, 60 mM sodium acetate, 10 mM dithiothreitol, and 10 mM magnesium acetate were heated to 100° C. for one minute, cooled to 25° C. for one minute, and treated with 2 units Klenow fragment for two minutes. The cycle of heating, cooling and adding Klenow was repeated 19 times. A ten-μl aliquot was removed from the reaction mixture and subjected to a further ten cycles of amplification using each of the primers:

d(CAGACACCATGGTGCACCTGACTCCTG)
and d(CCCCACAGGGCAGTAACG-
GCAGACTTCTCC), which amplify a 58-bp fragment contained within the 110-bp fragment produced above. This final ten cycles of amplification was accomplished by diluting the 10-μl aliquot into 90 μl of the fresh Tris-acetate buffer described above containing 100 nanomoles each dNTP and 200 pmoles of each primer. Reaction conditions were as above. After ten cycles a 10-μl aliquot (corresponding to 100 nanograms of the original DNA) was applied to a 6% NuSieve (FMC Corp.) agarose gel and visualized using ethidium bromide.

Figure 10:
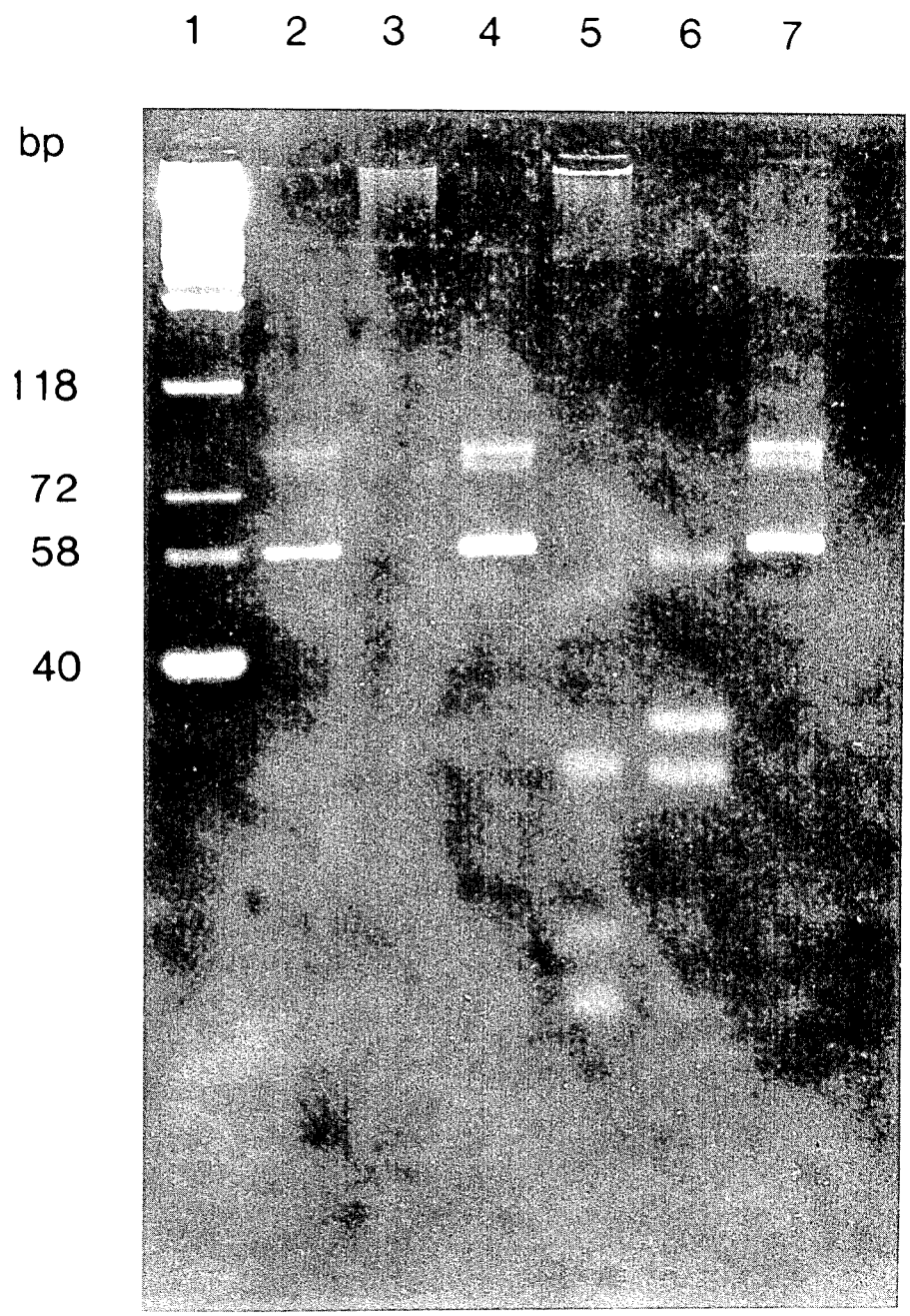
FIG. 10 illustrates a photograph of a 6% NuSieve agarose gel visualized using ethidium bromide and UV light. This photograph demonstrates amplfication of a sub-fragment of a 110-bp amplification product which sub-fragment is an inner nested set within the 110-bp fragment.

FIG. 10 illustrates this gel illuminated with UV light and photographed through a red filter as is known in the art. Lane 1 is molecular weight markers. Lane 2 is an aliquot of the reaction described above. Lane 3 is an aliquot of a reaction identical to that described above, except that the original wild-type DNA was cleaved with DdeI prior to amplification. Lane 4 is an aliquot of a reaction identical to that described above, except that human DNA homozygous for the sickle betaglobin allele was treated with DdeI prior to amplification (the sickle allele does not contain a DdeI site in the fragment being amplified here). Lane 5 is an aliquot of a reaction identical to that described above, except that salmon sperm DNA was substituted for human DNA. Lane 6 is an aliquot of a reaction identical to that described above, except that the aliquot was treated with DdeI after amplification (DdeI should convert the 58-bp wild-type product into 27-and 31-bp fragments). Lane 7 is an aliquot of the Lane 4 material treated with DdeI after amplification (the 58-bp sickle product contains no DdeI site).

Detection of a 58-bp fragment representative of a singlecopy gene from one microgram of human DNA using only ethidium bromide staining of an agarose gel requires an amplification of about 500,000fold. This was accomplished by using the two nested sets of oligonucleotide primers herein. The first set amplified the 110-bp fragment and the inner nested set amplifies a subfragment of this product up to the level of convenient detection shown in FIG. 10. This procedure of using primers amplifying a smaller sequence contained within the sequence being amplified in the previous amplification process and contained in the extension products of the other primers allows one to distinguish the wild-type from the sickle allele at the betaglobin locus without resorting to either radioisotopic or non-radioisotopic probe hybridization methodology such as that of Conner et al., Proc. Natl. Acad. Sci. USA, 80:278 (1983) and Leary et al., Proc. Natl. Acad. Sci USA, 80:4045 (1983).

EXAMPLE 11

The present process is expected to be useful in detecting, in a patient DNA sample, a specific sequence associated with an infectious disease such as, e.g., Chlamydia using a biotinylated hybridization probe spanning the desired amplified sequence and using the process described in U.S. Pat. No. 4,358,535, supra. The biotinylated hybridization probe may be prepared by intercalation and irradiation of a partially double-stranded DNA with a 4'-methylene substituted 4,5'-8-trimethylpsoralen attached to biotin via a spacer arm of the formula:

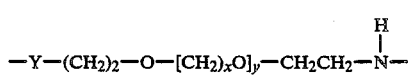

where Y is O, NH or N-CHO, x is a number from 1 to 4, and y is a number from 2 to 4, as described in U.S. Pat. Nos. 4,582,789 issued Apr. 15, 1986, and 4,617,261 reissued Oct. 14, 1986, the disclosures of which are incorporated herein by reference. Detection of the biotinyl groups on the probe may be accomplished using a streptavidin-acid phosphatase complex commercially obtainable from Enzo Biochemical using the detection procedures suggested by the manufacturer in its brochure. The hybridized probe is seen as a spot of precipitated stain due to the binding of the detection complex, and the subsequent reaction catalyzed by acid phosphatase, which produces a precipitable dye.

EXAMPLE 12

In this example, the process of Example 7 was basically used to amplify a 119 base pair fragment on the human β-hemoglobin gene using the primers:

5'-CTTCTGcagCAACTGTGTTCACTAGC-3' (GH18)

5'-CACaAgCTTCATCCACGTTCACC-3' (GH19)

where lower case letters denote mismatches from wild-type sequence to create restriction enzyme sites. The full scheme is shown in Table I. Table I illustrates a diagram of the primers GH18 and GH19 which are used for cloning and sequencing a 119-base pair fragment of the human β-globin gene and which are designed to contain internal restriction sites. The start codon ATG is underlined. GH18 is a 26-base oligonucleotide complementary to the negative strand and contains an internal PstI site. GH19 is a 23-base oligonucleotide complementary to the plus strand and contains an internal HindIII recognition sequence. Arrows indicate the direction of extension by DNA polymerase I. The boxed sequences indicate the restriction enzyme recognition sequences of each primer. These primers were selected by first screening the regions of the gene for homology to the PstI and HindIII restriction sites of bacteriophage M13. The primers were then prepared as described in previous examples.

TABLE I

```
                                                DdeI

GH19
                                     <——————————CCACTTGCACCTAC TTCgAa CAC
CTTCTGACACAACTGTGTTCACTAGCAACCTCAAACAGACACCATGGTGCACCTGACTCC
             TGAGGAGAAGTCTGCCGTTACTGCCCTGTGGGGCAAGGTGAACGTGGATGAAGTTGGTG(+)
GAAGACTGTGTTGACACAAGTGATCGTTGGAGTTTGTCTGTGGTACCACGTGGACTGAGG
                         ACTCCTCTTCAGACGGCAATGACGGGACACCCCGTTCCACTTGCACCTACTTCAACCAC(-)
CTTCTG cagCAA CTGTGTTCACTAGC——————————>
          GH18

Pst I
5' CTTCTG cagCAA CTGTGTTCACTAGC 3'   GH18 left linker primer

5' CAC aAgCTT CATCCACGTTCACC     3'   GH19 right linker primer
       Hind III
```

Amplification and Cloning

After twenty cylces of amplification of 1 microgram of human genomic DNA isolated from the cell line Molt 4 as described in Example 2, 1/14h of the reaction product was hybridized to the labeled β-globin specific oligonucleotide probe, RS06, of the sequence 5'-globin CTGACTCCTGAGGAGAAGTCTGCCGT-TACTGCCCTGTGGG-3' using the methods described above for oligomer restriction. Following solution hybridization, the reaction mixture was treated with DdeI under restriction digestion conditions as described above, to produce an 8-bases pair oligonucleotide. The amount of this 8-base pair product is proportional to the amount of amplified product produced. The digestion products were resolved on a 30% polyacrylamide gel and visualized by autoradiography.

Analysis of the autoradiogram revealed that the amplification was comparable in efficiency to that of amplification with primers PC03 (5'-ACACAACTGTGTTCACTAGC-3') and PC04 (5'-CCACTTGCACCTACTTCAAC-3'), which are complementary to the negative and positive strands, respectively, of the wild-type β-globin.

The amplified product was ethanol precipitated to desalt and concentrate the sample, redissolved in a restriction buffer of 10 mM Tris pH 8, 10 mM MgCl₂, 1 mM DTT, 100 mM NaCl₂, and simultaneously digested with PstI and HindIII. After digestion the sample was desalted with a Centricon 10 concentrator and ligated overnight at 12° C. with 0.3 micrograms of the PstI/-HindIII digested vector M13mp10w, which is publicly available from Boehringer-Mannheim.

The entire ligation mixture was transformed into E. coli strain JM103, which is publicly available from BRL in Bethesda, MD. The procedure followed for preparing the transformed strain is described in Messing, J. (1981) *Third Cleveland Symposium on Macromolecules: Recombinant DNA*, ed. A. Walton, Elsevier, Amsterdam, 143–153.

The transformation mixture was plated onto x-gal media for screening via plaque hybridization with nylon filters. The filters were probed with a β-globin-specific oligonucleotide probe RS24 of the sequence 5'-CCCACAGGGCAGTAACGGCAGACTTCTCCT-CAGGAGTCAG-3' to determine the number of β-globin inserts. The filters were then reprobed with the prime PC04 to determine the total number of inserts.

Plating and Screening

Table II summarizes the plating and plaque hybridization data. The filters were probed with the primer PC04 to determine the percentage of inserts resulting from amplification and cloning; 1206 clear plaques (90% of total number of clear plaques) hybridized to the primer. Fifteen plaques hybridized to the β-globin specific probe RS24. The percentage of β-globin positive plaques among the amplified primer-positive plaques is approximately 1%.

TABLE II

| Plate No. | Blue Plaques | No Inserts* | Inserts** | β-Globin Inserts |
|---|---|---|---|---|
| 1 | 28 | 25 | 246 | 1 |
| 2 | 29 | 18 | 222 | 2 |
| 3 | 11 | 26 | 180 | 0 |
| 4 | 24 | 20 | 192 | 5 |
| 5 | 22 | 27 | 185 | 5 |
| 6 | 39 | 21 | 181 | 3 |
| TOTAL | 158 | 132 | 1206 | 15 |

% of plaques containing amplified sequences which contain β-globin insert = 15/1206 × 100 = 1.24%
% of total plaques which contain β-globin insert = 15/1496 × 100 = ca. 1%
% of total plaques which contain amplified sequences = 1206/1496 × 100 = 0.8%
*Clear plaques which do not hybridize to primer PC04
**Clear plaques which hybridize to primer PC04

Restriction Enzyme and Southern Blot Analysis

DNAs from phage DNA minipreparation of three β-globin positive and two β-globin negative (but PC04 primer positive) plaques were analyzed by restriction enzyme analysis. MstII digestion of DNA from M13 clones containing the amplified β-globin fragment should generate a characteristic 283 base-pair fragment. Following MstII digestion, the three β-globin positive clones all produced the predicted 283 base pair fragment, while the two clones which were positive only with the primer produced larger fragments.

The gel from this analysis was transferred to a MSI nylon filter and hybridized with a radiolabeled nick-translated β-globin probe prepared by standard nick translation methods as described by Rigby et al., *J. Mol. Biol.* (1977), 113:237–51. The only bands which hybridized to the β-globin probe were the three β-globin positive clones. The two other clones had inserts which did not hybridize to the β-globin probe.

Sequence Analysis

The β-globin positive clones which were shown by restriction enzyme analysis to contain the β-globin insert were sequenced using the M13-dideoxy sequencing method. Of the ten clones, nine were identical to the β-globin wild-type sequence. The other clone was identical to the ∂-blobin gene which had been shown to be amplified to only a small degree by the β-globin primers.

In conclusion, the modified linker primers were nearly as efficient as the unmodified primers in amplifying the β-globin sequence. The primers were able to facilitate insertion of amplified DNA into cloning vectors. Due to the amplification of other segments of the genome, only 1% of the clones contained hemoglobin sequences.

Nine of the ten clones were found to be identical to the published β-globin sequence, showing that the technique amplifies genomic DNA with high fidelity. One clone was found to be identical with the published β-globin sequence, confirming that the primers are specific for the β-globin gene despite their having significant sequence homology with β-globin.

When cloning was carried out with a 267 base pair fragment of the β-globin gene, cloning was effective only when dimethylsulfoxide was present (10% by volume at 37° C.) in the amplification procedure.

Restriction site-modified primers were also used to amplify and clone and partially sequence the human N-ras oncogene and to clone 240-base pair segments of the HLA DQ-α and DQ-β genes. All of these amplifications were carried out in the presence of 10% by volume dimethylsulfoxide at 37° C. The primers for amplifying HLA DQ-α and DQ-β genes were much more specific for their intended targets than were the β-globin and DR-β primers, which, rather than giving a discrete band on an ethidium bromide stained agarose gel, produced only a smear. In addition, the HLA DQ-α primers produced up to 20% of clones, with amplified inserts which contained the desired HLA target fragment, whereas 1% of the β-globin clones contained the target sequence. The HLA DQ-α and DQ-β gene cloning was only effective when the DMSO was present and the temperature was elevated.

EXAMPLE 13

This example illustrates the use of the process herein to prepare the TNF gene of 494 base pairs starting from two oligonucleotides of 74 base pairs each.

PRIMERS

The primers employed were prepared by the method described in Example 2 and are identified below, each being 74 mers.

(TN10) 5'-CCTCGTCTACTCCCAGGTCCTCTTCAAGGGCCAAGGCTGCC

CCGACTATGTGCTCCTCACCCACACCGTCAGCC—3'

(TN11) 5'-GGCAGGGGCTCTTGACGGCAGAGAGGAGGTTGACCTTCTCC
                                    TGGTAGGAGATGGCGAAGCGGCTGACGGTGTGG—3'

(LL09) 5'-CCTGGCCAATGGCATGGATCTGAAAGATAACCAGCTGGTGG
                                    TGCCAGCAGATGGCCTGTACCTCGTCTACTCCC—3'

(LL12) 5'-CTCCCTGATAGATGGGCTCATACCAGGGCTTGAGCTCAGCC
                                    CCCTCTGGGGTGTCCTTCGGGCAGGGGCTCTTG—3'

(TN08) 5'-TGTAGCAAACCATCAAGTTGAGGAGCAGCTCGAGTGGCTGA
                                    GCCAGCGGGCCAATGCCCTCCTGGCCAATGGCA—3'

(TN13) 5'-GATACTTGGGCAGATTGACCTCAGCGCTGAGTTGGTCACCC
                                    TTCTCCAGCTGGAAGACCCCTCCCTGATAGATG—3'

(LL07) 5'-CCTTAAGCTTATGCTCAGATCATCTTCTCAAAACTCGAGTG
                                    ACAAGCCTGTAGCCCATGTTGTAGCAAACCATC—3'

(TN14) 5'-GCTCGGATCCTTACAGGGCAATGACTCCAAAGTAGACCTGC
                                    CCAGACTCGGCAAAGTCGAGATACTTGGGCAGA—3'

OVERALL PROCEDURE

I. Ten cycles of the protocol indicated below were carried out using primers TN10 and TN11, which interact as shown in the diagram below, step (a).

II. A total of 2 μl of the reaction mixture from Part I above was added to the primers LL09 and LL12. The protocol described below was carried out for 15 cycles, so that the primers would interact with the product of Part I as shown in the diagram below, step (b).

III. A total of 2 μl of the reaction mixture from Part II above was added to the primers TN08 and TN13. The protocol described below was carried out for 15 cycles, so that the primers would interact with the product of Part II as shown in the diagram below, step (c).

IV. A total of 2 μl of the reaction mixture from Part III above was added to he primers LL07 and LL14. The protocol described below was carried out for 15 cycles, so that the primers would interact with the product of Part III as shown in the diagram below, step (d).

PROTOCOL

Each reaction contained 100 μl of:
2 mM of each of dATP, dCTP, dGTP and TTP
3 μM of each of the primers used at that step
1×polymerase buffer, (30 mM Tris-acetate, 60 mM Na-acetate, 10 mM Mg-acetate, 2.5 mM dithiothreitol)
Each cycle constituted:
1. 1 min. in boiling water
2. 1 min. cooling at room temperature
3. add 1 μl (5 units) of the Klenow fragment of DNA polymerase
4. allow the polmerization reaction to proceed for 2 min. For the next cycle start again at step 1.

DIAGRAM

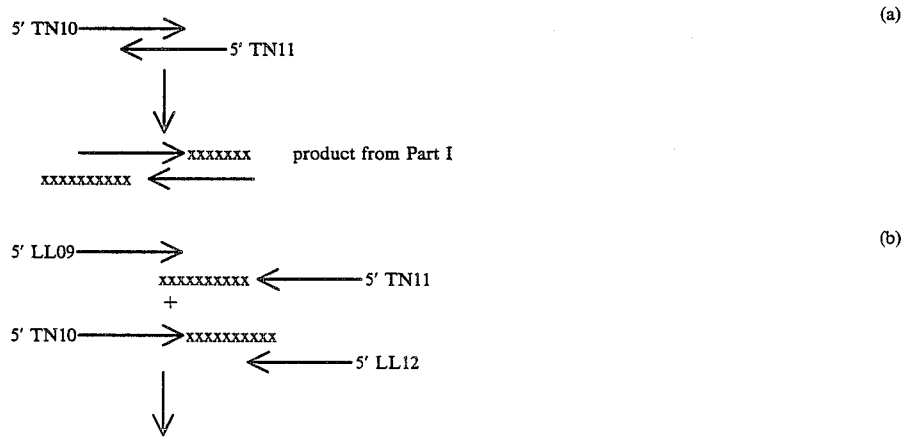

-continued
DIAGRAM

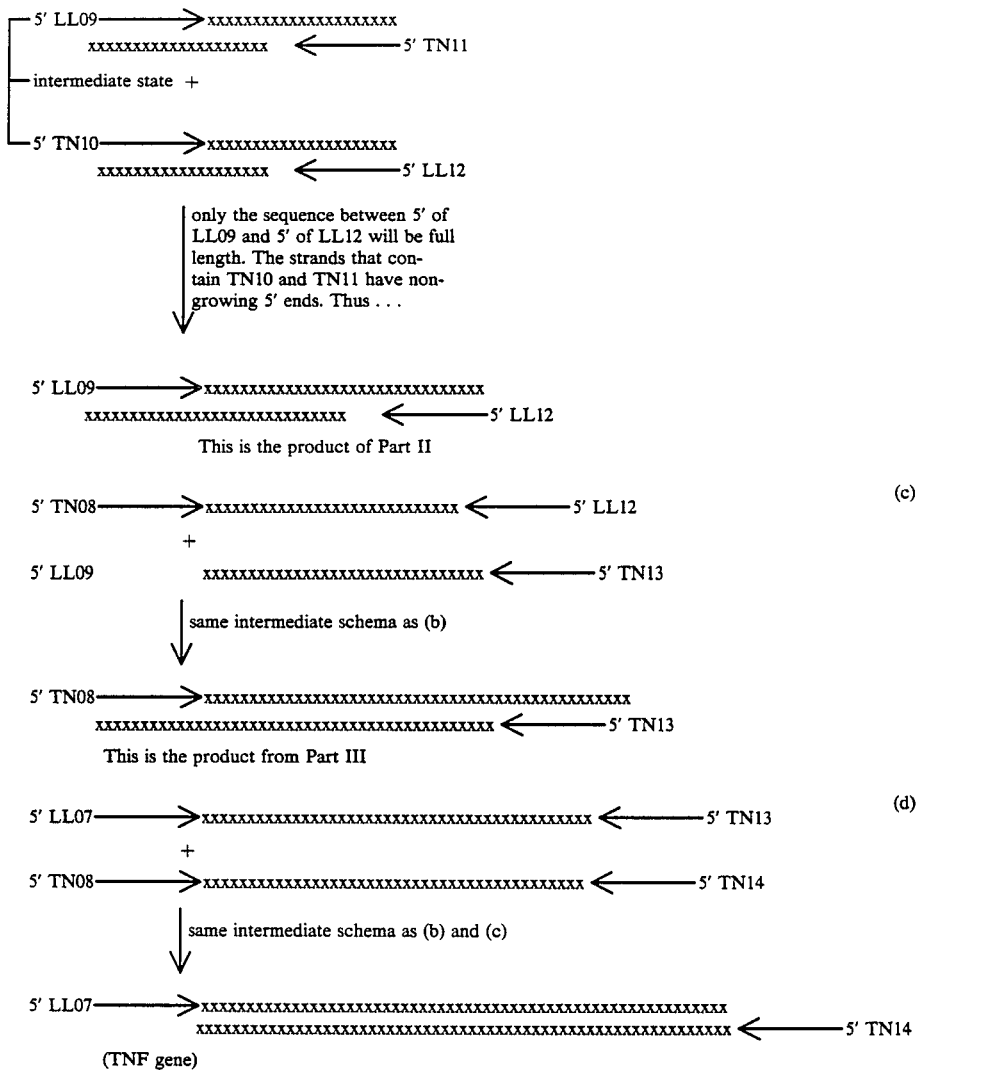

(TNF gene)

Deposit of Materials

The cell line SC-1 (CTCC #0082) was deposited on Mar. 19, 1985 with the American Type Culture Collection (ATCC), 12301 Parklawn Drive, Rockville, Md. 20852 USA, with ATCC Accession No. CRL#8756. The deposit of SC-1 was made pursuant to a contract between the ATCC and the assignee of this patent application, Cetus Corporation. The contract with ATCC provides for permanent availability of the progeny of this cell line to the public on the issuance of the U.S. patent describing and identifying the deposit or the publications or upon the laying open to the public of any U.S. or foreign patent application, whichever comes first, and for availability of the progeny of this cell line to one determined by the U.S. Commissioner of Patents and Trademarks to be entitled thereto according to 35 CFR §122 and the Commissioner's rules pursuant thereto (including 37 CFR §1.14 with particular reference to 886 OG 638). The assignee of the present application has agreed that if the cell line on deposit should die or be lost or destroyed when cultivated under suitable conditions, it will be promptly replaced on notification with a viable culture of the same cell line.

In summary, the present invention is seen to provide a process for detecting sequences in nucleic acids by first amplifying one or more specific nucleic acid sequences using a chain reaction in which primer extension products are produced which can subsequently act as templates for further primer extension reactions. The process is especially useful in detecting nucleic acid sequences which are initially present in only very small amounts. Also, the amplification process can be used for molecular cloning.

Other modifications of the above described embodiments of the invention which are obvious to those of skill in the area of molecular biology and related disciplines are intended to be within the scope of the following claims.

What is claimed is:

1. A process for cloning into a vector a specific nucleic acid sequence contained in a nucleic acid or a mixture of nucleic acids, which process comprises:
   a. treating the nucleic acid(s) with one oligonucleotide primer for each strand of each different specific sequence being amplified, under conditions such that for each strand of each different sequence being amplified an extension product of wherein said primer or primers are selected so as to be sufficiently complementary to each strand of each specific sequence to hybridize therewith such that the extension product synthesized from one primer, when it is separated from its complement, can serve as a template for synthesis of the extension product of the other primer, and wherein said primer or primers each contain a restriction site on its 5' end which is the same as or different from the restriction site(s) on the other primer(s);

b. separating the primer extension products from the templates on which they were synthesized to produce single-stranded molecules;

c. treating the single-stranded molecules generated from step (b) with oligonucleotide primers such that a primer extension product is synthesized using each of the single strands produced in step (b) as a template, wherein depending on the particular sequence being amplified, steps (a) and (c) are carried out in the presence of from 0 to 10% dimethylsulfoxide or at a temperature of 35° C. to 45° C.

d. adding to the product of step (c) a restriction enzyme for each of said restriction sites to obtain cleaved products in a restriction digest; and e. ligating the cleaved product(s) into one or more cloning vectors.

2. The process of claim 1, further comprising the step of passing the restriction digest of step (d) through a desalting column before step (e).

3. The process of claim 1, further comprising, after step (e), sequencing the specific nucleic acid sequence.

4. The process of claim 1, further comprising, after step (e), expressing the protein encoded by the specific nuclei acid sequence.

5. The process of claim 1, wherein one sequence is being amplified, the restriction sites are different on each primer, and the product of step (d) is ligated into a cloning vector with a specific orientation.

6. The process of claim 1, wherein the specific nucleic acid sequence being amplified is or is contained within the $\beta$-globin gene or the N-RAS oncogene.

* * * * *

UNITED STATES PATENT AND TRADEMARK OFFICE
CERTIFICATE OF CORRECTION

PATENT NO. : 4,800,159

DATED : January 24, 1989

INVENTOR(S) : Kary B. Mullis, Henry A. Erlich, Norman Arnheim, Glenn T. Horn, Randall K. Saiki, and Stephen J. Scharf It is certified that error appears in the above-identified patent and that said Letters Patent is hereby corrected as shown below:

Column 1, line 10, change "nuclei" to --nucleic--.
Column 5, line 36, change "sickel" to --sickle--.
Column 5, line 62, change "sickel" to --sickle--.
Column 6, line 2, change "HinFfI" to --HinfI--.
Column 7, line 37, change "amlified" to --amplified--.
Column 8, line 36, change "nuclei" to --nucleic--.
Column 12, line 13, change "taht" to --that--.
Column 12, line 25, change "accumulates" to --accumulate--.
Column 15, line 21, change "an" to --can--.
Column 15, line 39, change ""CATgATCCGA . . ." to --"CAGgATCCGA . . .--.
Column 18, line 39, change "sickel" to --sickle--.
Column 18, line 50, change "sickel" to --sickle--.
Column 18, line 66, change "sickel" to --sickle--.
Column 19, line 5, change "sickel" to --sickle--.
Column 20, line 28, change "pBr322" to --pBR322--.
Column 21, line 35, change "ge." to --gel.--.
Column 22, line 4, change "set" to --site--.
Column 23, line 49, change "mumbers" to --numbers--.
Column 24, line 29, between "which" and "added" insert --was--.
Column 26, line 40, change "amplifier" to --amplified--.
Column 26, line 59, change "nM" to --mM--.
Column 32, line 64, change "8-bases" to --8-base--.

UNITED STATES PATENT AND TRADEMARK OFFICE
CERTIFICATE OF CORRECTION

PATENT NO. : 4,800,159

DATED : January 24, 1989

INVENTOR(S) : Kary B. Mullis, Henry A. Erlich, Norman Arnheim, Glenn T. Horn, Randall K. Saiki, and Stephen J. Scharf It is certified that error appears in the above-identified patent and that said Letters Patent is hereby corrected as shown below:

Column 33, line 31, change "prime" to --primer--.
Column 34, line 18, change "δ-blobin" to --δ-globin--.
Column 34, line 34, change "β-globin" to --δ-globin--.
Column 35, line 44, change "he" to --the--.
Claim 1, column 39, line 3, between "of" and "wherein" insert --each primer is synthesized which is complementary to each nucleic acid strand,--.
Claim 4, column 40, line 15, change "nuclei" to --nucleic--.

Signed and Sealed this

Twenty-sixth Day of September, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,800,159
DATED : January 24, 1989
INVENTOR(S) : Kary B. Mullis et al.

It is certified that error appears in the above-identified patent and that said Letters Patent is hereby corrected as shown below:

<u>Title page,</u>
Item [*] Notice, should read:
-- [*] Notice: This patent is subject to a Terminal Disclaimer. --

Signed and Sealed this

Ninth Day of December, 2003

JAMES E. ROGAN
*Director of the United States Patent and Trademark Office*